US012590936B2

(12) United States Patent (10) Patent No.: US 12,590,936 B2
Potyrailo et al. (45) Date of Patent: Mar. 31, 2026

(54) MULTI-FREQUENCY SENSING SYSTEM AND METHOD

(71) Applicant: General Electric Company, Schenectady, NY (US)

(72) Inventors: Radislav Alexandrovich Potyrailo, Niskayuna, NY (US); Janell Marie Crowder, Clifton Park, NY (US); Richard St. Pierre, Clifton Park, NY (US); Baokai Cheng, Niskayuna, NY (US)

(73) Assignee: GE Infrastructure Technology LLC, Greenville, SC (US)

( * ) Notice: Subject to any disclaimer, the term of this patent is extended or adjusted under 35 U.S.C. 154(b) by 427 days.

(21) Appl. No.: 18/116,174

(22) Filed: Mar. 1, 2023

(65) Prior Publication Data

US 2024/0295536 A1 Sep. 5, 2024

(51) Int. Cl.
*G01N 33/00* (2006.01)
*G01N 27/27* (2006.01)

(52) U.S. Cl.
CPC ..... *G01N 33/0073* (2013.01); *G01N 33/0006* (2013.01); *G01N 33/0062* (2013.01); *G01N 33/0068* (2024.05)

(58) Field of Classification Search
CPC ........... G01N 33/0073; G01N 33/0006; G01N 33/0062; G01N 33/0068; G01N 27/27
See application file for complete search history.

(56) References Cited

U.S. PATENT DOCUMENTS

| | | | |
|---|---|---|---|
| 4,457,161 A | 7/1984 | Iwanaga et al. | |
| 5,320,814 A | 6/1994 | Walt et al. | |
| 5,345,213 A | 9/1994 | Semancik et al. | |
| 6,010,616 A | 1/2000 | Lewis et al. | |
| 6,235,243 B1 | 5/2001 | Fleischer et al. | |
| 6,960,476 B2 | 11/2005 | Morris | |
| 9,995,593 B2 | 6/2018 | Badeja et al. | |
| 11,428,658 B2 | 8/2022 | Carbonelli et al. | |
| 2004/0026268 A1 | 2/2004 | Maki et al. | |
| 2020/0292480 A1 | 9/2020 | Chrimes et al. | |

(Continued)

OTHER PUBLICATIONS

Laref et al., "Orthogonal Signal Correction to Improve Stability Regression Model in Gas Sensor Systems," Aug. 1, 2017, vol. 17, Hindawi, Journal of Sensors, 8 Pages.

(Continued)

*Primary Examiner* — Laura Martin
*Assistant Examiner* — Anthony W Megna Fuentes
(74) *Attorney, Agent, or Firm* — Fletcher Yoder, P.C.

(57) ABSTRACT

A sensor device may include an electrochemical (EC) gas sensor, a metal-oxide semiconductor (MOS) gas sensor, and control circuitry. The control circuitry may provide EC excitation signals to the EC gas sensor, provide at least two MOS excitation signals to the MOS gas sensor, and detect at least two gases. The control circuitry may detect the gases based on receiving EC response signals from the at least one EC gas sensor based on providing the EC excitation signals, receiving MOS response signals from the MOS gas sensor based on providing the MOS excitation signals, determining a multivariate response pattern based on the EC response signals and the MOS response signals, and differentiating between the at least two gases in contact with the sensor device based on the multivariate response pattern.

13 Claims, 10 Drawing Sheets

(56) References Cited

U.S. PATENT DOCUMENTS

2021/0278384 A1    9/2021    Potyrallo et al.
2022/0011283 A1    1/2022    Carbonelli et al.

OTHER PUBLICATIONS

Hagleitner et al., "Smart single-chip gas sensor microsystem," Nov. 15, 2001, Letters to Nature, vol. 414, pp. 293-296.

Persaud et al., "Analysis of discrimination mechanisms in the mammalian olfactory system using a model nose," Nature vol. 299, Sep. 23, 1982, pp. 352-355.

Beccherelli et al., "Design of a very large chemical sensor system for mimicking biological olfaction, " Nov. 24, 2009, Sensors and Actuators B 146 (2010), doi:10.1016/j.snb.2009.11.031 , pp. 446-452.

Bernabei et al., "Large-Scale Chemical Sensor Array Testing Biological Olfaction Concepts," IEEE Sensors Journal, vol. 12, No. 11, Nov. 2012, pp. 3174-3183.

Marco et al., "A biomimetic approach to machine olfaction, featuring a very large-scale chemical sensor array and embedded neuro-bio-inspired computation," Dec. 21, 2013, Microsyst Technol, DOI 10.1007/s00542-013-2020-8 , 14 Pages.

Ulmer et al., "Sensor arrays with only one or several transducer principles? The advantage of hybrid modular systems," May 6, 1999, Sensors and Actuators B 65 (2000), pp. 79-81.

Jin et al., "Evaluation of Multitransducer Arrays for the Determination of Organic Vapor Mixtures," Jan. 1, 2008, vol. 80, No. 1, Analytical Chemistry, pp. 227-236.

Jin et al., "Limits of Recognition for Binary and Ternary Vapor Mixtures Determined with Multitransducer Arrays," Oct. 1, 2008, vol. 80, No. 19, Analytical Chemistry, pp. 7283-7293.

Pardo et al., "Data analysis for a hybrid sensor array," Jul. 2, 2004, Sensors and Actuators B 106 (2005), pp. 136-143.

Jin et al., "A Comparison of Multi-Transducer Arrays and Single-Transducer Arrays for the Determination of Multi-Vapor Mixtures," IEEE Sensors 2007 Conference, pp. 1217-1220.

Scholten et al., "Vapor Discrimination with Single- and Multitransducer Arrays of Nanoparticle-Coated Chemiresistors and Resonators," Jun. 2013, vol. 13, No. 6, IEEE Sensors Journal, pp. 2146-2154.

Ni et al., "Orthogonal gas sensor arrays with intelligent algorithms for early warning of electrical fires," Nov. 17, 2007, Sensors and Actuators B 130 (2008), pp. 889-899.

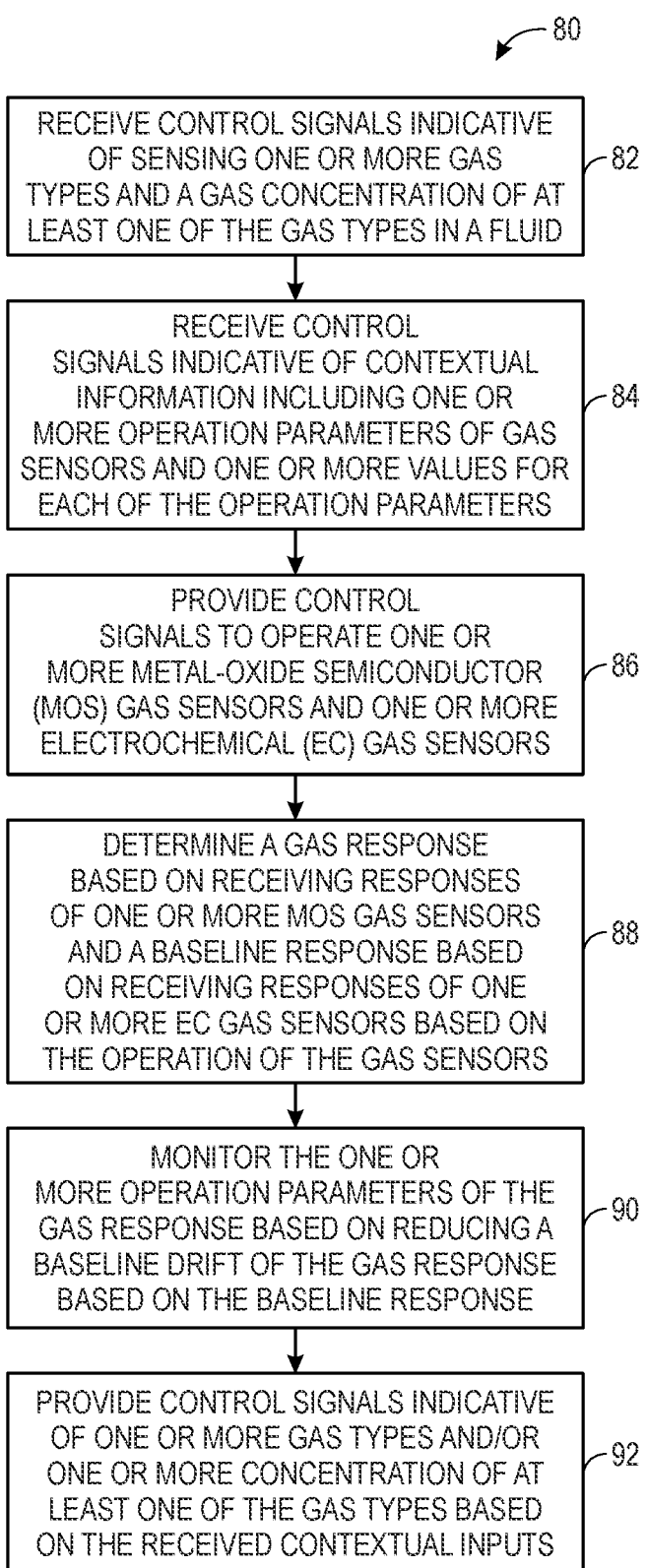

```
                                                    ┌─ 80

┌─────────────────────────────────────────┐
│       RECEIVE CONTROL SIGNALS INDICATIVE   │
│          OF SENSING ONE OR MORE GAS        │──── 82
│     TYPES AND A GAS CONCENTRATION OF AT    │
│    LEAST ONE OF THE GAS TYPES IN A FLUID   │
└─────────────────────────────────────────┘
                      │
                      ▼
┌─────────────────────────────────────────┐
│              RECEIVE CONTROL               │
│    SIGNALS INDICATIVE OF CONTEXTUAL        │
│      INFORMATION INCLUDING ONE OR          │──── 84
│   MORE OPERATION PARAMETERS OF GAS         │
│   SENSORS AND ONE OR MORE VALUES FOR       │
│    EACH OF THE OPERATION PARAMETERS        │
└─────────────────────────────────────────┘
                      │
                      ▼
┌─────────────────────────────────────────┐
│              PROVIDE CONTROL               │
│        SIGNALS TO OPERATE ONE OR           │
│    MORE METAL-OXIDE SEMICONDUCTOR          │──── 86
│    (MOS) GAS SENSORS AND ONE OR MORE       │
│      ELECTROCHEMICAL (EC) GAS SENSORS      │
└─────────────────────────────────────────┘
                      │
                      ▼
┌─────────────────────────────────────────┐
│          DETERMINE A GAS RESPONSE          │
│       BASED ON RECEIVING RESPONSES         │
│     OF ONE OR MORE MOS GAS SENSORS         │
│      AND A BASELINE RESPONSE BASED         │──── 88
│       ON RECEIVING RESPONSES OF ONE        │
│    OR MORE EC GAS SENSORS BASED ON         │
│     THE OPERATION OF THE GAS SENSORS       │
└─────────────────────────────────────────┘
                      │
                      ▼
┌─────────────────────────────────────────┐
│             MONITOR THE ONE OR             │
│    MORE OPERATION PARAMETERS OF THE        │
│   GAS RESPONSE BASED ON REDUCING A         │──── 90
│   BASELINE DRIFT OF THE GAS RESPONSE       │
│     BASED ON THE BASELINE RESPONSE         │
└─────────────────────────────────────────┘
                      │
                      ▼
┌─────────────────────────────────────────┐
│   PROVIDE CONTROL SIGNALS INDICATIVE       │
│    OF ONE OR MORE GAS TYPES AND/OR         │
│   ONE OR MORE CONCENTRATION OF AT          │──── 92
│   LEAST ONE OF THE GAS TYPES BASED         │
│    ON THE RECEIVED CONTEXTUAL INPUTS       │
└─────────────────────────────────────────┘
```

*FIG. 3*

MULTI-FREQUENCY SENSING SYSTEM AND METHOD

GOVERNMENT LICENSE RIGHTS

This invention was made with Government support under Agreement number W15QKN-18-9-1004 awarded by ACC-NJ to the CWMD Consortium. The Government has certain rights in the invention.

FIELD

One or more embodiments are disclosed that relate to systems and methods for sensing gases.

BACKGROUND

Gas sensors may be based on sensing materials that include metal oxide semiconductor (MOS) materials, dielectric polymers, conducting polymers, nanotubes, metal organic frameworks, graphene, supramolecular compounds, and some others.

Conventional MOS sensors have a relatively narrow dynamic range of measurements due to the nature of the interaction mechanisms of MOS sensing materials with the ambient environment. While MOS materials may have commercial success because of their broad applications for gas alarms in residential and industrial facilities, the readout of MOS materials is conventionally performed by measuring resistance change of the material as a function of gas concentration. Such a relationship follows a well-known power law, with saturation of sensor response occurring at high concentrations. Conventional single-output sensors measuring values and/or induced changes on resistance, capacitance, electrical current, light intensity, and other changes of a single output are known as zero-order analytical instruments.

BRIEF DESCRIPTION

In one or more embodiments, a sensor device is described. The sensor device may include an electrochemical (EC) gas sensor, a metal-oxide semiconductor (MOS) gas sensor, and control circuitry. The control circuitry may provide a first one or more excitation signals to the EC gas sensor, provide a second one or more excitation signals to the MOS gas sensor at a first alternating current (AC) excitation frequency, provide a third one or more excitation signals to the MOS gas sensor at a second AC excitation frequency. The control circuitry may detect a first gas (or fluid) based on receiving a first one or more excitation signal responses in response to providing the first one or more excitation signals to the EC gas sensor, and receiving a second one or more excitation signal responses in response to providing the second one or more excitation signals to the MOS gas sensor. Moreover, the control circuitry may detect a second gas based on receiving the first one or more excitation signal responses, and receiving a third one or more excitation signal responses in response to providing the third one or more excitation signals to the MOS gas sensor.

In another embodiment, another sensor device is described. The sensor device may include a metal-oxide semiconductor (MOS) gas sensor and control circuitry. The control circuitry may provide a first one or more excitation signals to the MOS gas sensor at a first alternating current (AC) excitation frequency, provide a second one or more excitation signals to the MOS gas sensor at a second AC excitation frequency, provide a third one or more excitation signals to the MOS gas sensor at a third AC excitation frequency, and detect a first gas, a second gas, and a third gas based on excitation signal responses of the MOS gas sensor in response to providing the first one or more excitation signals, the second one or more excitation signals, and the third one or more excitation signals.

In yet another embodiment, a method is described. The method is performed by a processor of a sensor device. The method includes receiving first control signals indicative of sensing one or more gas types (or fluid types), providing second control signals indicative of providing first excitation signals to a metal-oxide semiconductor (MOS) gas sensor and providing second excitation signals to an electrochemical (EC) gas sensor, determining a gas response based on receiving excitation signal responses of the MOS gas sensor, determining a baseline response based on receiving excitation signal responses of the EC gas sensor, and providing third control signals indicative of detecting at least two gas types in contact with the sensor device and a concentration of at least one of the at least two gas types to one or more output devices based on the gas responses and the baseline responses.

BRIEF DESCRIPTION OF THE DRAWINGS

FIG. 3 illustrates a process for determining one or more gas types, at least a concentration of one of the gas types, or both, by the sensor system of FIG. 1, in accordance with one embodiment;

DETAILED DESCRIPTION

One or more embodiments of the subject matter described herein provide sensing systems and methods that allow for differentiation between different gases.

Figure 1:
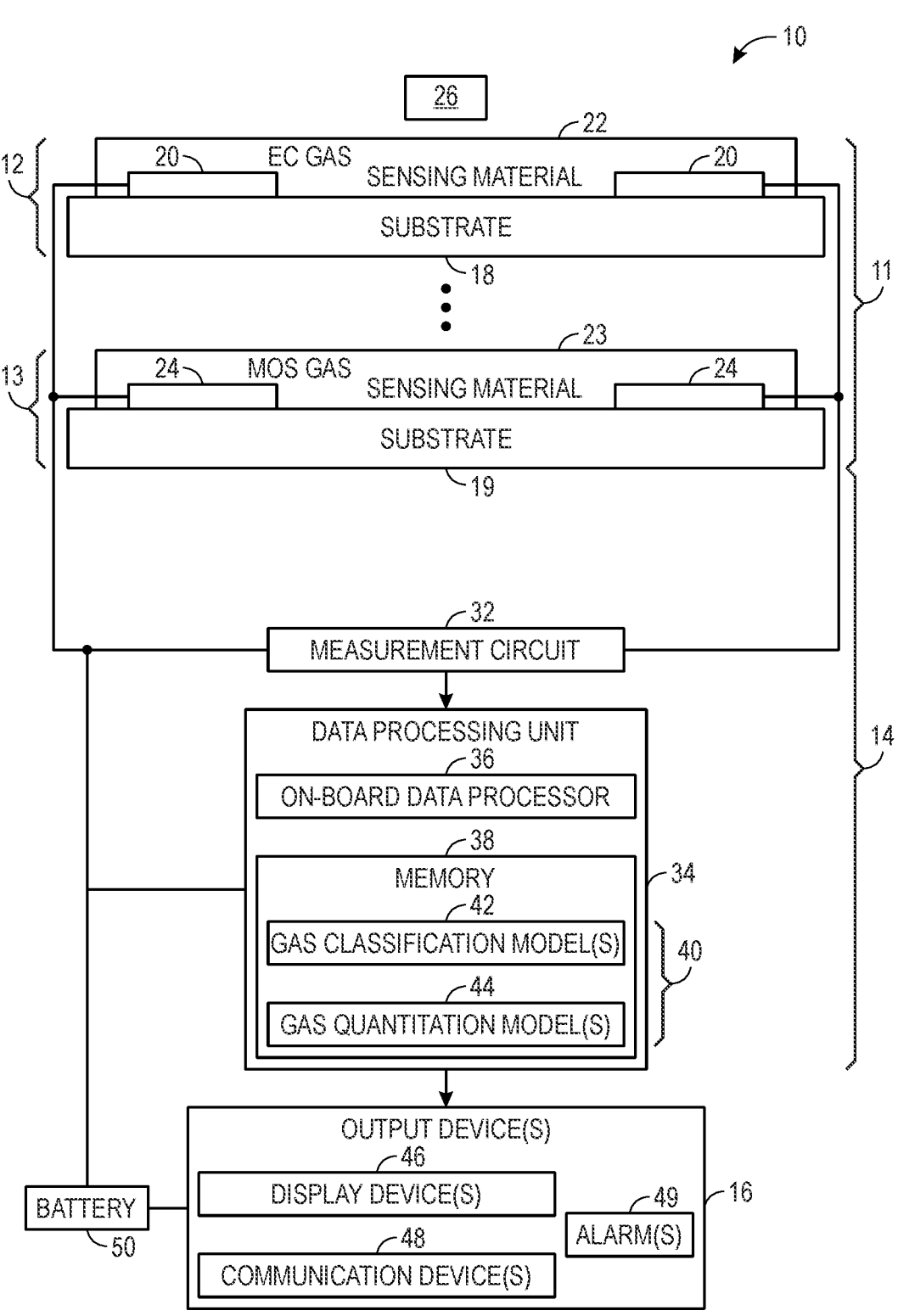
FIG. 1 illustrates a sensor system including at least one metal-oxide semiconductor (MOS) gas sensor and at least one electrochemical (EC) gas sensor, in accordance with one embodiment.

FIG. 1 is a schematic diagram of an embodiment of a gas sensor 10 (e.g., a sensor system) for multi-gas analysis of fluid samples, in accordance with the present technique. In different embodiments, the gas sensor 10 may be a wearable multi-gas sensor, an ingestible gas sensor for personal (e.g., patient) monitoring, and so forth. In certain embodiments, the gas sensor 10 may be an industrial environmental sensor, an asset monitoring sensor, an industrial process monitoring gas sensor, a consumer sensor, a transportation sensor, a security sensor, or any combination thereof. In further embodiments, the sensor may be part of a wireless sensor network.

The gas sensor 10 may include an array 11 of sensors, control circuitry 14, and one or more output devices 16. The control circuitry 14 includes a measurement circuit 32 and a data processing unit 34. In the depicted embodiment, the array 11 includes an electrochemical (EC) sensing element 12 (e.g., EC sensing element 12) and a metal oxide semiconductor (MOS) sensing element 13 (e.g., MOS sensing element 13). It should be appreciated that in alternative or additional embodiments, the array 11 may include any number and/or combination of viable sensors. For example, the array 11 may include multiple EC gas sensing elements 12, multiple MOS gas sensing elements 13, or any combination of both, among other things. The MOS gas sensing element 13 also is known as semiconducting metal oxide (SMOX) gas sensor and also is known as semiconducting metal oxide (MOX) gas sensor.

In some embodiments, excitation or dielectric excitation of the MOS gas sensing element 13 refers to an alternating current (AC) excitation of the MOS gas sensing element 13 at a shoulder of its dielectric relaxation region. The dielectric excitation or AC excitation of the MOS gas sensing element 13 may be based on including a MOS gas sensing material 23, or another non-MOS sensing material such as dielectric polymer material, conducting polymer material, nanotubes material nanowires material, nanoparticles material, metal organic frameworks material, graphene material, supramolecular compound material, a MXene which is a two-dimensional inorganic material consisting of atomically thin layers of transition metal carbides, nitrides, or carbonitrides, and/or other materials.

The EC gas sensing element 12 may include a substrate 18, electrodes 20 disposed on the substrate 18, and an EC gas sensing material 22 disposed on the substrate 18 in contact with the electrodes 20. The sensor 10 may include one or more temperature sensors, one or more humidity sensors, and one or more pressure sensors, among other sensors. The measurement circuit 32 may include a voltage controller and an electrical current detector electrically coupled to the electrodes 20. The voltage controller may include a direct current (DC) voltage source, an AC voltage source, or both. In specific cases, the DC voltage source may provide excitation signals to the EC gas sensing element 12 and the AC voltage source may provide excitation signals to the MOS gas sensing element 13. As such, the measurement circuit 32 may provide one or more excitation signals (e.g., a bias voltage) across the electrodes 20 during multi-gas analysis of a fluid 26. Moreover, the measurement circuit 32 may measure electrical current response and/or a DC response of the EC gas sensing material 22 and measure impedance response and/or an AC response of the MOS gas sensing material 23.

The responses of the EC gas sensing material 22 may be indicative of identities and/or concentrations of gases present in the fluid 26. The electrical current responses (e.g., the impedance response, the DC response, the AC response, among other things) of the EC gas sensing element 12 may be collectively and/or interchangeably referred to as one or more excitation responses (or excitation signal responses). The measurement circuit 32 may differentiate gases in the fluid 26 by analyzing the excitation responses of the EC gas sensing element 12 to the fluid 26.

Similarly, the MOS gas sensing element 13 may include a substrate 19 and electrodes 24 disposed on the substrate 18. The MOS gas sensing element 13 may include MOS gas sensing materials 23 disposed on the substrate 19 between and/or over the electrodes 24. In some cases, each of the electrodes 24 may include a number of interdigitated sensing electrodes. In such cases, the MOS gas sensing material 23 may generally form a gas sensing film with the electrodes 24. As such, dielectric excitation of the MOS gas sensing material 23 and measurement of dielectric excitation responses of the gas sensing material 23 is performed via the electrodes 24. The electrodes 24 of the MOS gas sensing element 13 may be electrically coupled to the measurement circuit 32 or any other viable excitation and measurement circuitry. As such, the measurement circuit 32 may provide one or more excitation signals to the electrodes 24 and measure the excitation responses of the electrodes 24 during the multi-gas analysis of the fluid 26. Moreover, in some cases, the substrate 19 may include different materials compared to the substrate 18 discussed above.

The excitation responses may indicate the induced changes on the EC gas sensing material 22 and/or the MOS gas sensing material 23 as a function of gas concentration of the fluid 26. In specific cases, such a relationship may follow a well-known power law, with saturation of excitation responses occurring at high concentrations. The control circuitry 14 may measure induced changes on the EC gas sensing material 22 and/or the MOS sensing material 23 upon receiving the excitation responses. For example, the control circuitry 14 may measure electrical current, impedance, real part of impedance, imaginary part of impedance, admittance, reactance, susceptance, capacitance, electrical current, light intensity, or a combination thereof, among other things of the excitation responses. As used herein, "impedance" is a non-limiting term for measuring induced changes on the excitation signals when measuring the excitation responses.

The data processing unit 34 may apply a transfer function, a multiplier coefficient, a lookup table, a model, among other things, to data collected from the impedance response and/or the DC response of the EC gas sensing material 22 to identify one or more gases and/or concentration of gases present in the fluid 26. In some cases, the control circuitry 14 may include circuitry to detect multiple gases in the fluid 26 by performing measurements at AC and/or DC measurement conditions and/or impedance measurement conditions. Accordingly, the control circuitry 14 may determine gases (and/or concentration of gases) present in the fluid sample 26 based on the measured responses of the EC gas sensing element 12 and MOS gas sensing element 13 by the measurement circuit 32.

With the foregoing in mind, the measurement circuit 32 may provide the excitation signals to the electrodes 20 of the EC gas sensing element 12 and the electrodes 24 of the MOS gas sensing element 13 simultaneously, at relatively close times, or at different times to perform the multi-gas analysis of the fluid 26. In some cases, the excitation responses of the EC gas sensing elements 12 may be more stable in various environmental conditions over time while the MOS gas sensing elements 13 may receive excitation signals (e.g., stimuli) and return excitation responses at multiple frequencies (multiple ranges of frequencies). For example, the EC gas sensing elements 12 may be less susceptible to corrosion or environmental damages.

Accordingly, in some embodiments, the data processing unit 34 may generate a baseline response (e.g., a relatively constant response, a relatively stable response) based on the excitation responses of one or more of the EC gas sensing elements 12. Moreover, the data processing unit 34 may generate a gas response by correcting the excitation responses of one or more of the MOS gas sensing elements 13 at one or multiple frequencies based on the generated baseline response. For example, the data processing unit 34 may reduce a baseline drift of the gas responses by correcting the excitation responses of the MOS gas sensing elements 13 based on the excitation responses of the EC gas sensing elements 12.

The measurement circuit 32 may provide alternating current excitation signals to the MOS gas sensing material 23 at one or more preselected frequencies (e.g., preselected frequency ranges). The preselected frequencies may include one or multiple frequencies selected based on empirical and/or simulated sensor response data to perform the multi-gas analysis of the fluid 26. For example, a preselected frequency may include a frequency at the shoulder of dielectric relaxation region of the MOS sensing material 23. Moreover, the measurement circuit 32 may monitor the excitation responses (or gas-modulated excitation signals) of the MOS sensing material 23 at the preselected frequencies. In specific embodiments, the measurement circuit 32 may additionally or alternatively provide one or more DC excitation signals to the MOS gas sensing material 23 and measure the DC responses (e.g., resistance responses) of the MOS gas sensing material 23 to these excitations.

In some embodiments, the measurement circuit 32 may provide multiple excitation signals to the MOS sensing material 23 at multiple preselected frequencies (e.g., frequency ranges). For example, the excitation responses of the MOS sensing material 23 may be monitored at a gas-modulated high-frequency shoulder of the dielectric relaxation peak of the MOS sensing material 23, a gas-modulated low-frequency shoulder of the dielectric relaxation peak of the MOS sensing material 23, among other frequencies. In such embodiments, the measurement circuit 32 may include circuitry to receive multiple excitation responses of the MOS sensing material 23 at the multiple preselected frequencies.

Moreover, the measurement circuit 32 may measure one or more parameters of the excitation responses at the multiple preselected frequencies. The one or more parameters may include changes induced by measurements of impedance at different frequencies, changes induced by temperature of the sensing elements 12 and/or 13, and/or changes induced by UV or visible light (known as photoactivation) applied to the sensor. Determining such induced changes of the multiple excitation responses may indicate the gases and/or concentration of gases in the fluid 26.

For example, the measurement circuit 32 may measure such parameters based on comparing the excitation responses with the corresponding excitation signals. Moreover, different operation parameters may be selected for different sensor arrays 10 and/or based on an application of a sensor array 10. Furthermore, in different embodiments, the measurement circuit 32 may monitor and/or determine a different number and/or combination of operation parameters.

The gas sensor 10 may represent one or more different versions of multi-gas sensing systems described herein. In one or more embodiments, the measurement circuit 32 may include a number of resistor-capacitor (RC) circuits to measure the induced impedance changes of a number of the multiple excitation responses. Each of the RC circuits may include one or more resistors (R) and/or capacitors (C). In specific embodiments, one or more of the RC circuits may include one or more variable resistors and/or capacitors. In such embodiments, the data processing unit 34 may electronically control a value of the variable resistors and/or capacitors of an RC circuit. For example, the data processing unit 34 may control the value of the variable resistors and/or capacitors based on a desired frequency for generating and/or measuring an excitation signal. Moreover, in some cases, the data processing unit 34 may control the value of the variable resistors and/or capacitors based on one or more analyte gases of interest.

Accordingly, the measurement circuit 32 may generate and provide multiple excitation signals to the MOS gas sensing material 23 and measure multiple excitation responses of the MOS gas sensing material 23 at multiple frequencies. In any case, the measurement circuit 32 is not designed to be affected by the measured gas concentrations. Rather, only the EC sensing element 12 and the MOS gas sensing element 13 are designed to be predictably affected by the measured gas concentrations.

The data processing unit 34 may receive the excitation responses (e.g., data bits, digital responses (counts), analog responses) measured by the measurement circuit 32. The data processing unit 34 may include an on-board data processor 36 and a memory 38, among other things. The memory 38 may store gas analysis models 40, such as gas classification models 42 and gas quantitation models 44. These gas analysis models 40 are mathematical models that generally store relationships between excitation responses (e.g., dielectric excitation responses) and particular classifications or concentrations of gases in the fluid 26. For example, the gas classification models 42 may store relationships between excitation responses of the EC gas sensing material 22 and/or MOS gas sensing material 23 and particular classifications of gases.

Moreover, the gas quantitation models 44 may store relationships between excitation responses of the EC gas sensing material 22 and/or MOS gas sensing material 23 and particular concentrations of gases. In specific embodiments, the gas analysis models 40 may include one or more coefficients having values that are experimentally determined (e.g., empirical data, simulation data, among other things) and stored in the memory 38. In some embodiments, the number of analyte gases determined by the gas classification models 42, or gas quantitation models 44, or any combination thereof, for the illustrated gas sensor 10 may range from two analyte gases to fifty analyte gases.

A gas sensor that provides two or more excitation responses or outputs is called a multivariable gas sensor. The data processing unit 34 may apply multivariate data processing principles to analyze outputs from a multivariable gas sensor. For example, the data processing unit 34 may apply multivariate data processing principles to the output signals to determine one or more multivariate response pattern. Accordingly, the data processing unit 34 may quantify diversity of responses of a multivariable sensor to different gases. In some cases, multivariate transfer functions can be built to quantify different gases. The built multivariate transfer functions can be implemented to quantify different gases in new measurement data from this multivariable gas sensor.

Non-limiting examples of multivariate data processing principles include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis algorithms include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Non-limiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), Support Vector Regression (SVR) or Artificial Neural Network Analysis (ANN). In certain aspects of the inventive subject matter described herein, a classification algorithm can be followed by quantitation algorithm.

As discussed below, the on-board data processor 36 may receive the excitation responses measured by the measurement circuit 32, select particular excitation responses, and provide the selected excitation responses as inputs to one or more of the stored gas analysis models 40 for analysis. The gas analysis models 40 may return outputs that resolve or differentiate two or more gases in the fluid 26. As used herein, "resolving" two or more gases in the fluid 26, "providing resolution" between two or more gases in the fluid 26, "differentiating" two or more gases in the fluid 26, or "providing differentiation" between two or more gases in the fluid 26 refers to determining a respective classification for each of the gases in the fluid 26, determining a respective concentration of the gases in the fluid 26, or determining both respective classifications and respective concentrations of gases in the fluid 26. As used herein, "classifying" or "determining a classification of" a gas refers to determining a chemical identity (e.g., ethanol, acetone, hydrogen, carbon monoxide, methane, toluene, benzene, among other chemical gas identities) of the gas or determining a chemical class (e.g., a hydrocarbon, an oxide, a sulfide, a ketone, an aromatic hydrocarbon, and so forth) to which each gas belongs.

For example, the fluid 26 may be in the form of a fluid vessel that may be a form of a vessel with controlled volume, or in the form of an open area such as an indoor facility (e.g., a room, a hall, a house, a school, a hospital, a confined space, or the like), or in the form of an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, a city, urban environment, marine environment, battlefield environment or the like). In one embodiment, the gas sensor 10 may provide continuous monitoring of the fluid 26 within the reservoir or flow path. In one or more embodiments, the gas sensor 10 may be an impedance gas sensor, an electromagnetic sensor, an electronic sensor, a hybrid sensor, or another type of sensor. The gas sensor 10 may be a sensor array.

The fluid 26 may include, for example, a gas, a liquid, a gas-liquid mixture, a solid material, particles or particulate matter, or the like, containing one or more gases, including analyte gases and/or interferent gases. In another embodiment, the fluid 26 may be a gas or fuel, such as a hydrocarbon-based fuel. For example, the fluid 26 may be natural gas or hydrogen gas that is supplied to a powered system (e.g., a manned vehicle, an unmanned vehicle, an airplane engine, or a stationary generator set) for consumption. Further, the fluid 26 may include gasoline, diesel fuel, jet fuel or kerosene, bio-fuels, petrodiesel-biodiesel fuel blends, natural gas (liquid or compressed), and/or fuel oils. In other embodiments, the fluid 26 may be a sample of indoor or outdoor ambient air. For example, the sample may be from an industrial, residential, military, construction, urban, or any other known site. Further, the ambient air sample may include relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical agents such as nerve, blister, blood, and choking agents, hydrocarbons and/or other environmental agents.

In other embodiments, the fluid 26 may be a disinfecting agent, such as alcohol, aldehyde, chlorine dioxide, hydrogen peroxide, and so forth. In other embodiments, the fluid 26 may mix with ambient air from around the gas sensor 10 with relatively small concentrations, medium concentrations, and/or large concentrations of combustible gases such as methane, ethane, propane, butane, hydrogen, and/or other gases. The ambient air may have certain measurable or identifiable characteristics, such as relative humidity, temperature, barometric pressure, concentrations of other gases, etc. In further embodiments, the fluid 26 may include at least one gas dissolved in an industrial liquid such as transformer oil, bioprocess media, fermentation media, wastewater, and so forth. The fluid 26 may also include at least one gas dissolved in a consumer liquid such as milk, a non-alcoholic beverage, alcoholic beverage, cosmetics, and so forth. In other embodiments, the fluid 26 may include at least one gas dissolved in a body liquid such as blood, sweat, tears, saliva, urine, feces, bile, and so forth.

In certain embodiments, the fluid 26 may include analyte gases that are toxic industrial materials or toxic industrial chemicals. A non-limiting list of example toxic industrial materials and chemicals includes, but is not limited to, ammonia, arsine, boron trichloride, boron trifluoride, carbon disulfide, chlorine, diborane, ethylene oxide, fluorine, form-aldehyde, hydrogen bromide, hydrogen chloride, hydrogen cyanide, hydrogen fluoride, hydrogen sulfide, nitric acid (fuming), phosgene, phosphorus trichloride, sulfur dioxide, sulfuric acid, and tungsten hexafluoride.

Moreover, in certain embodiments, the fluid 26 may include analyte gases that are toxic materials of the medium Hazard Index. A non-limiting list of example toxic materials of the medium Hazard Index include, for example, Acetone cyanohydrin, Acrolein, Acrylonitrile, Allyl alcohol, Allylamine, Allyl chlorocarbonate, Boron tribromide, Carbon monoxide, Carbonyl sulfide, Chloroacetone, Chloroacetonitrile, Chlorosulfonic acid, Diketene, 1,2-Dimethylhydrazine, Ethylene dibromide, Hydrogen selenide, Methanesulfonyl chloride, Methyl bromide, Methyl chloroformate, Methyl chlorosilane, Methyl hydrazine, Methyl isocyanate, Methyl mercaptan, Nitrogen dioxide, Phosphine, Phosphorus oxychloride, Phosphorus pentafluoride, Selenium hexafluoride, Silicon tetrafluoride, Stibine, Sulfur trioxide, Sulfuryl chloride, Sulfuryl fluoride, Tellurium hexafluoride, n-Octyl mercaptan, Titanium tetrachloride, Trichloroacetyl chloride, and Trifluoroacetyl chloride The fluid 26 may include analyte gases that are toxic materials of the "high" hazard index. A non-limiting list of example toxic materials of the high Hazard Index may include, for example, Ammonia, Arsine, Boron trichloride, Boron trifluoride, Carbon disulfide, Chlorine, Diborane, Ethylene oxide, Fluorine, Formaldehyde, Hydrogen bromide, Hydrogen chloride, Hydrogen cyanide, Hydrogen fluoride, Hydrogen sulfide, Nitric acid, fuming, Phosgene, Phosphorus trichloride, Sulfur dioxide, Sulfuric acid, and Tungsten hexafluoride.

In certain embodiments, the fluid 26 may include analyte gases that are toxic materials of the low Hazard Index. A non-limiting list of example toxic materials of the low Hazard Index includes, but is not limited to: Allyl isothiocyanate, Arsenic trichloride, Bromine, Bromine chloride, Bromine pentafluoride, Bromine trifluoride, Carbonyl fluoride, Chlorine pentafluoride, Chlorine trifluoride, Chloroacetaldehyde, Chloroacetyl chloride, Crotonaldehyde, Cyanogen chloride, Dimethyl sulfate, Diphenylmethane-4,40-diisocyanate, Ethyl chloroformate, Ethyl chlorothioformate, Ethyl phosphonothioic dichloride, Ethyl phosphonic dichloride, Ethyleneimine, Hexachlorocyclopentadiene, Hydrogen iodide, Iron pentacarbonyl, Isobutyl chloroformate, Isopropyl chloroformate, Isopropyl isocyanate, n-Butyl chloroformate, n-Butyl isocyanate, Nitric oxide, n-Propyl chloroformate, Parathion, Perchloromethyl mercaptan, sec-Butyl chloroformate, tert-Butyl isocyanate, Tetraethyl lead, Tetraethyl pyrophosphate, Tetramethyl lead, Toluene 2,4-diisocyanate, and Toluene 2,6-diisocyanate. Analyte gases may also include a range of indoor environmental agents, such as Acetaldehyde, Formaldehyde, 1,3-Butadiene, Benzene, Chloroform, Methylene chloride, 1,4-Dichlorobenzene, Perchloroethylene, Trichloroethylene, Naphthalene, Polycyclic aromatic compounds, as well as outdoor environmental agents, such as Ozone, Nitrogen dioxide, Sulfur dioxide, Carbon monoxide. Further, the analyte gases may include industrial agents, such as combustibles, confined space hazards, and so forth.

In certain embodiments, the fluid 26 may include analyte gases that are indoor pollutants. A non-limiting list of example indoor pollutants includes, but is not limited to: acetaldehyde, formaldehyde, 1,3-butadiene, benzene, chloroform, methylene chloride, 1,4-dichlorobenzene, perchloroethylene, trichloroethylene, naphthalene, and polycyclic aromatic compounds. In certain embodiments, the fluid 26 may include analyte gases that are outdoor pollutants. A non-limiting list of example outdoor pollutants includes, but is not limited to: ozone, nitrogen dioxide, sulfur dioxide, and carbon monoxide.

Embodiments of the gas sensor 10 have the ability to differentiate gases at different concentrations in the fluid 26. For example, the gas sensor 10 may differentiate analyte gases at regulated vapor-exposure limits established by different organizations. In specific embodiments, the gas sensor 10 can resolve analyte gases below a Permissible Exposure Limit (PEL). In some embodiments, the gas sensor 10 can resolve analyte gases below Threshold Limit Value Short-Term Exposure Limit (TLV-STEL). In some embodiments, the gas sensor 10 may resolve analyte gases below Threshold Limit Value Time-Weighted Average (TLV-TWA). In some embodiments, the gas sensor 10 may resolve analyte gases below Immediately Dangerous to Life or Health (IDLH). In specific embodiments, the gas sensor 10 may resolve analyte gases below and above Lower Explosive Limit (LEL). In specific embodiments, the gas sensor 10 may be capable of resolving gases having a concentration less than 5%, less than 100 part-per-million (ppm), less than 100 part-per-billion (ppb), less than 100 part-per-trillion (ppt).

In any case, in some embodiments, the memory 38 may be integrated into the on-board data processor 36. Moreover, in some alternative or additional embodiments, the on-board data processor 36 may include a multicore processor. For example, the on-board data processor 36 may include a multicore processor on a single integrated circuit with two or more separate processing units (also referred to as cores), each of which may read and execute program instructions. In yet alternative or additional embodiments, the multicore processor may only include a single central processing unit (CPU) and multiple additional cores. For embodiments in which the on-board data processor 36 is a multicore processor, different gas analysis models and/or different signal processing algorithms may be independently executed by different cores to reduce the power consumption of the data processing unit 34 and/or the gas sensor 10.

In the illustrated embodiment, the gas sensor 10 may also include one or more output devices 16. In some embodiments, the output devices 16 include one or more display devices 46 that are configured to present information regarding a multi-gas analysis. For example, the display devices 46 may display the classification and/or concentration of two or more gases in the fluid 26. In alternative or additional embodiments, the output devices 16 may include alarms 49, such as visual alarms (e.g., light emitting diodes (LEDs)), auditory alarms (e.g., speakers), and/or haptic alarms (e.g., haptic feedback devices).

Alternatively or additionally, the output devices 16 may include one or more communication devices 48 (e.g., wired communication interfaces, wireless communication interfaces) that may enable the gas sensor 10 to communicate with other computing systems, such as a desktop computer, a mobile computing device (e.g., a laptop, smart phone), a remote server (e.g., an Internet server, a cloud server), or other sensors (e.g., gas sensors, temperature sensors, vibration sensors, health monitors) of a multi-sensor monitoring system. For example, in some embodiments, information determined by the on-board data processor 36 regarding the differentiation of two or more gases in the fluid 26 may be provided to an external computing system that serves as a controller of a mesh of sensors that includes the gas sensor 10. In some embodiments, the gas sensor 10 may additionally or alternatively use the communication devices 48 to provide excitation response measurements to an external computing system, such that the external computing system can use these measurements to calculate one or more coefficient values for one or more of the gas analysis models and return these coefficient values to the gas sensor 10 for storage in the memory 38.

Additionally, the illustrated gas sensor 10 includes a battery 50 that is electrically coupled to various components of the gas sensor 10 to supply electrical power. In the depicted embodiment, the battery 50 is coupled to the control circuitry 14 and the output devices 16. It may be appreciated that the battery 50 should have a suitable electrical energy storage capacity to power all of the components of the gas sensor 10 coupled thereto. For example, the battery 50 may include sufficient electrical energy storage capacity for heating the gas sensing material 22, providing DC excitation to the EC gas sensing material 22, providing dielectric/AC excitation to the MOS gas sensing material 23, measuring the excitation responses of the gas sensing materials 22 and 23, analyzing the measured excitation responses to differentiate two or more gases in the fluid 26, and presenting results of the analysis via the output devices 16.

In certain embodiments, the battery 50 may has a capacity that is sufficient to operate the gas sensor 10 for at least 6 hours, 10 hours, 15 hours, 24 hours, 48 hours, and so on. In some embodiments, the battery 50 may have a battery capacity between 1 milliamp-hour (mAh) and 50,000 mAh, between 1 mAh and 10,000 mAh, or between 1 mAh and 100 mAh. In certain embodiments, such as embodiments in which the gas sensor 10 is designed to be particularly thin (e.g., for ingestible or tattooed embodiments of the gas sensor 10), the battery 50 may have a thickness less than about 5 millimeters (mm). In some embodiments, all of the components of the gas sensor 10 may be coupled to or at least partially disposed within a suitable packaging or housing for a particular gas sensing application. For example, for personal monitoring applications, the packaging of the gas sensor 10 may be made of a biocompatible polymer that can be externally worn, subcutaneously injected, or ingested to perform personal or patient multi-gas analysis.

The gas sensor 10 may be a wearable device that may be worn or move from one place to another by an operator. The gas sensor 10 may be positioned in or be an integrated part of a helmet, hat, glove, or other clothing attributes. For example, the gas sensor 10 may be held within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a fabric of the clothing, can be positioned on clothing such as on a pocket, can be in a form of an arm band, worn on a wrist or other extremity, or the like. The wearable device may be worn by a subject, such as a human, animal, or a robot. The wearable device may be removably coupled or integrated with an article worn by a subject (e.g., a shirt, pants, safety vest, safety personal protection clothing, eyeglasses, hat, helmet, hearing device, or the like), or may be any alternative device that may be transferrable such that sensor can be moved between different positions, may be stationary or substantially stationary, or the like.

The wearable device may be worn, or otherwise carried, by different subjects or individuals, such as, but not limited to, soldiers, medical professionals, athletes, system operators, students, otherwise active or inactive individuals, or the like. Optionally, the wearable sensing system may be coupled with, integrated with, disposed on, or the like, an asset, such as a moving system such as a drone, a stationary system, or the like. The wearable systems may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like. The wearable device can be fabricated using manufacturing technologies based on complementary metal-oxide semiconductor electronics, flexible electronics, flexible hybrid electronics and other known approaches to provide conformal and flexible designs, implementations, and use. Optionally, the gas sensor 10 may be a stationary device, may be independently mobile (e.g., detachable from an operator and capable of moving independent of the operator), may be airborne, or the like.

Figure 2:
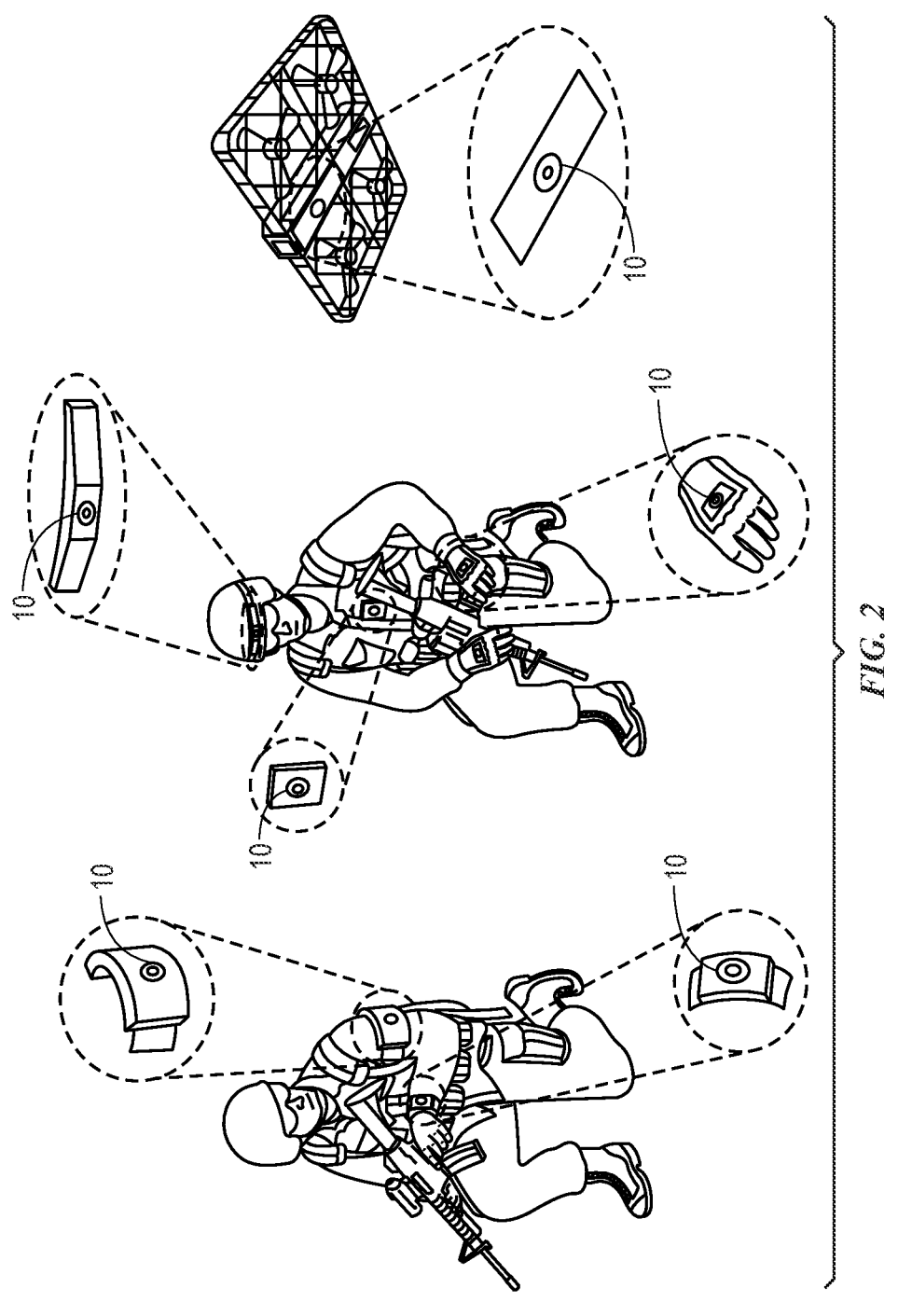
FIG. 2 illustrates example positions of a wearable sensor system, in accordance with one embodiment.

In one or more embodiments, the gas sensor 10 may be a handheld sensor system. In one or more embodiments, the gas sensor 10 may be a wearable sensor system, may be held within a wearable and/or non-wearable transferrable object (e.g., a frame of military or industrial eyeglasses), or the like. The wearable device may be worn by a subject, such as a human or animal, may be removably coupled or integrated with an article worn by a subject (e.g., a shirt, pants, safety vest, safety personal protection clothing, eyeglasses, hat, helmet, hearing device, or the like), or may be any alternative device that may be transferrable such that sensor can be moved between different positions, may be stationary or substantially stationary, or the like. FIG. 2 illustrates example positions of different wearable gas sensors 10. In the illustrated embodiment of FIG. 2, the subject is a human subject, however the subject may be a mammal subject, a plant subject, or the like.

FIG. 2 illustrates example positions of different gas sensors 10. In the example embodiments of FIG. 2, multiple example implementations of the gas sensor 10 on a human subject and a drone is illustrated. However, FIG. 2 depicts only a few implementations of the gas sensor 10 and in alternative cases the subject may be different such as a mammal subject, a plant subject, or the like.

In one or more embodiments, the gas sensor 10 may be a wearable device worn by a subject, such as a human or an animal. Specifically, FIG. 2 illustrates non-limiting examples of positions of the gas sensing system for detection of a combustible gas or any other gas or vapor of interest using a single gas sensor 10. FIG. 2 demonstrates various positions a wearable gas sensor 10 may be worn. For example, the wearable gas sensor 10 may be worn directly on the body of a subject. Alternatively, the wearable gas sensor 10 may be removably coupled or integrated with an article worn by a subject. For example, as illustrated in FIG. 2, the wearable gas sensor 10 may be worn on military or industrial headgear, on a shirt sleeve, or on the front of a shirt or jacket or vest.

Additionally, the wearable gas sensor 10 may be worn on the hand or wrist, either directly on the body or integrated on a glove, as depicted in FIG. 2. Alternatively, the wearable gas sensor 10 may be removably coupled or integrated with a non-wearable transferrable object, such as an unmanned vehicle, for example on an unmanned ground or aerial or other vehicles. In this way, the wearable gas sensor 10 may be coupled or integrated with any alternative object or device that may be transferrable such that the gas sensor 10 can be moved between different positions, may be stationary or substantially stationary, or the like. Although not shown in FIG. 2, the wearable sensor may also be removable coupled or integrated with eyeglasses, pants, a safety vest, safety personal protection clothing, a hat, a hearing device, or any other wearable device or article of clothing. In the illustrated embodiment of FIG. 2, the subject is a human subject, however the subject may be a mammal subject, a plant subject, a robot subject, or the like.

FIG. 3 is a process 80 for multi-gas detection operation of the gas sensor 10 including at least one EC gas sensing element 12 and at least one MOS gas sensing element 13. Although the process 80 is described in a particular order, the process blocks may be performed in any other viable order. Moreover, it should be appreciated that the process 80 is provided by the way of example, and in alternative or additional embodiments, the gas sensor 10 may perform additional, reduced, and/or different operations. Furthermore, although the operations are described as being performed by the on-board data processor 36, hereinafter processor 36, the operations may be performed by any other on-board or external viable processing circuit. Although operations of one MOS gas sensing element 13 and one EC gas sensing element 12 is described, the processor 36 may provide similar control signals to, receive responses from, and/or otherwise perform the operations on multiple MOS gas sensing elements 13 and/or multiple EC gas sensing elements 12.

At block 82, the processor 36 may receive control signals indicative of sensing one or more gas types (or fluid types) and a gas concentration of at least one of the gas types in the fluid 26. In some cases, the processor 36 may receive the control signals stored in the memory 38 (e.g., one or more lookup tables) or from any other viable source. In some embodiments, the control signals may indicate sensing each gas type or different gas types by providing stimulus signals to the MOS gas sensing element 13 at different frequencies. For example, each gas type may be associated with performing the measurements by providing stimuli within one or more specific frequency ranges.

At block 84, the processor 36 may receive control signals indicative of contextual information. For example, the contextual information may be indicative of one or more operation parameters of the gas sensors and one or more values for each of the operation parameters. The operation parameters may include measuring/monitoring changes of one or more dependent and/or independent parameters of the sensor responses. For example, the gas sensor 10 may include a temperature controller (e.g., a heater) to change a temperature (e.g., sweep the temperature, scan the temperature) of the MOS gas sensing element 13 during operation. Moreover, the operation parameters may include a real and/or an imaginary part of impedance, frequency, temperature, among other things, of the sensor responses. In some embodiments, the MOS gas sensing element 13 may monitor each of the operation parameters at multiple frequencies or frequency ranges.

In some embodiments, the processor 36 may apply contextual inputs for selection of expected application scenarios based on the gas response when receiving data bits (or analog signals) from the measurement circuit 32. Non-limiting examples of contextual inputs can include intended sensor uses as a certain wearable device or as a permanent installation. Contextual inputs may also include the expected gas concentration in a certain environment or the concentration of an analyte gas an operator may need to detect to ensure the environment is safe to occupy. Other contextual inputs may include a geographical area of the sensor use, a location based on Global Positioning System coordinates, particular rural or urban locations, and an elevation at a particular location. Other contextual inputs may include the type of sensing material being used or the type of analyte gas to be measured. For example, a first set of operation parameters may be selected based on the contextual inputs. The first set of operation parameters may include a selected operation voltage of a heating element of the gas sensor 10, two or more frequencies of dielectric excitation, and a selected capacitance of one or more capacitors of the measurement circuit 32.

The contextual information may also include one or more preselected (e.g., known) values for one or more operation parameter of the selected operation parameters. In some embodiments, the preselected values may include range of changes of one or more of the operation parameters to determine a gas type (or class) and/or a gas concentration. In alternative or additional embodiments, the preselected values may include threshold gas concentration values for performing a subsequent operation. For example, the subsequent operation may include issuing an alarm for higher/lower than a threshold concentration of one or more specific gas types. It should be appreciated that such contextual information may be application specific and the gas sensor 10 may include/receive different contextual information for different applications of the gas sensor 10.

At block 86, the processor 36 may provide control signals to operate one or more MOS gas sensing elements 13 and one or more EC gas sensing element 12. As mentioned above, operating a MOS gas sensing element 13 at multiple frequencies may provide additional information to the processor 36 for determining multiple gas types by a single sensor (or array of sensors). Accordingly, in some embodiments, the processor 36 may provide the control signals to the one or more MOS gas sensing elements 13 at multiple frequencies, as will be appreciated.

A baseline response of the sensor 10 is the response in clean environment (e.g., when in contact with a clean carrier gas) in the absence of measured gas or gases (e.g., the fluid 26). The baseline response of the sensor 10 is comprised of the baseline response of the one or more EC gas sensing element 12 and the baseline response of the one or more MOS gas sensing elements 13. During operation, values of the baseline responses of the EC gas sensing element 12 and the MOS gas sensing element 13 may undesirably change. Such changes in the baseline responses may lead to decreased accuracy of classification and quantitation results. As such, the baseline response of EC gas sensing element 12 can be utilized for correction of the baseline response of MOS gas sensing element 13.

For example, the processor 36 may correct the baseline response of MOS gas sensing element 13 by tracking the deviation of the baseline response of the MOS gas sensing element 13 from the baseline response of the EC gas sensing element 12. Moreover, the processor 36 may apply a correction factor to eliminate such deviation of the baseline response of the MOS gas sensing element 13. For example, the processor 36 may retrieve the correction factor from multiple correction factors stored in the memory 38 based on tracking the deviation of the baseline response of the MOS gas sensing element 13 from the baseline response of the EC gas sensing element 12. Alternatively or additionally, the processor 36 may determine (e.g., calculate) the correction factor based on tracking the deviation of the baseline response of the MOS gas sensing element 13 from the baseline response of the EC gas sensing element 12. Illustrative examples of a correction factor may include univariate baseline subtraction between the response of the EC gas sensing element 12 and the response of MOS gas sensing element 13, multivariate baseline subtraction between one or more responses of the EC gas sensing element 12 and the response of MOS gas sensing element 13, among other things.

With the foregoing in mind, at block 88, the processor 36 may determine a gas response based on receiving responses of the one or more MOS gas sensing elements 13 and a baseline response based on receiving responses of the one or more EC gas sensing element 12. For example, the processor 36 may determine the baseline response based on receiving responses of one or more auxiliary environmental sensors such as temperature sensors, humidity sensors, pressure sensors, among other sensors. Moreover, the processor 36 may determine the gas response based on receiving data bits (or analog signals) from the measurement circuit 32. Furthermore, in different embodiments, the processor 36 may determine the gas response of the MOS gas response 13, the EC gas sensing element 12, or both at a specific time (e.g., instance), at consecutive instances (e.g., periodically), or continuously. For example, the EC gas sensing element 12 may collect data amperometry, cyclic voltammetry, chrono-amperometry, or using any other viable EC sensor measurement method over a time period.

At block 90, the processor 36 may monitor the one or more operation parameters of the gas response based on reducing a baseline drift of the gas response based on the baseline response. As mentioned above, the EC gas sensing element 12 may be less susceptible to providing drifted responses over time. As such, the processor 36 may reduce the baseline drift of the MOS gas sensing elements 13 (at one or the multiple frequencies) based on the baseline response of the EC gas sensing element 12. Moreover, it should be appreciated that monitoring may include determining or calculating based on a received equation, comparing with respect to one or more of the received operation parameters and the respective values, among other things. In any case, as mentioned above, the processor 36 may correct the baseline response of MOS gas sensing element 13 by tracking the deviation of the baseline response of the MOS gas sensing element 13 from the baseline response of the EC gas sensing element 12.

At block 92, the processor 36 may provide control signals indicative of one or more gas types and/or one or more concentration of at least one of the gas types based on the received responses from the sensing elements 12 and/or 13 and from contextualized inputs. Moreover, additionally or alternatively, the processor 36 may generate control signals indicative of performing one or more responsive actions. The responsive actions may include generating one or more alerts, activation of a particular treatment or decontamination of a subject having the sensor device, optimization of logistics steps after the knowledge about the detected concentration of the gas, minimization of logistics steps after the knowledge about the detected concentration of the gas, activation of an emergency response, or a combination thereof. Moreover, the responsive actions may be in response to detecting higher/lower than a threshold concentration of one or more of the gas types, among other things. Furthermore, in some embodiments, the processor 36 may provide the control signals indicative of one or more gas types and/or one or more concentration of at least one of the gas types at a specific time (e.g., instance), at consecutive instances (e.g., periodically), or continuously.

For example, information from the readings of the MOS gas sensing elements 13 and the EC sensing element 12 can be implemented for informational purposes. Informational purposes can include visual, acoustic, and/or haptic or any other known alarms. Alarms can be produced or issued on the gas sensor 10 with the MOS gas sensing elements 13 and the EC gas sensing element 12. Alarms can be transmitted to a central station or can be transmitted to another gas sensor 10 with the similar or different MOS gas sensing elements 13 and/or EC gas sensing element 12. Alarms can be in the form of quantitative information such as the concentration of the detected gas. Alarms can be in the form of semi-quantitative information such as binned levels of the detected gas, for example three bins such as yellow, orange, and red levels of alarms. Alarms can be in the form of qualitative information such as alarm about the detected gas above a predetermined threshold of the concentrations of this gas.

Figure 4:
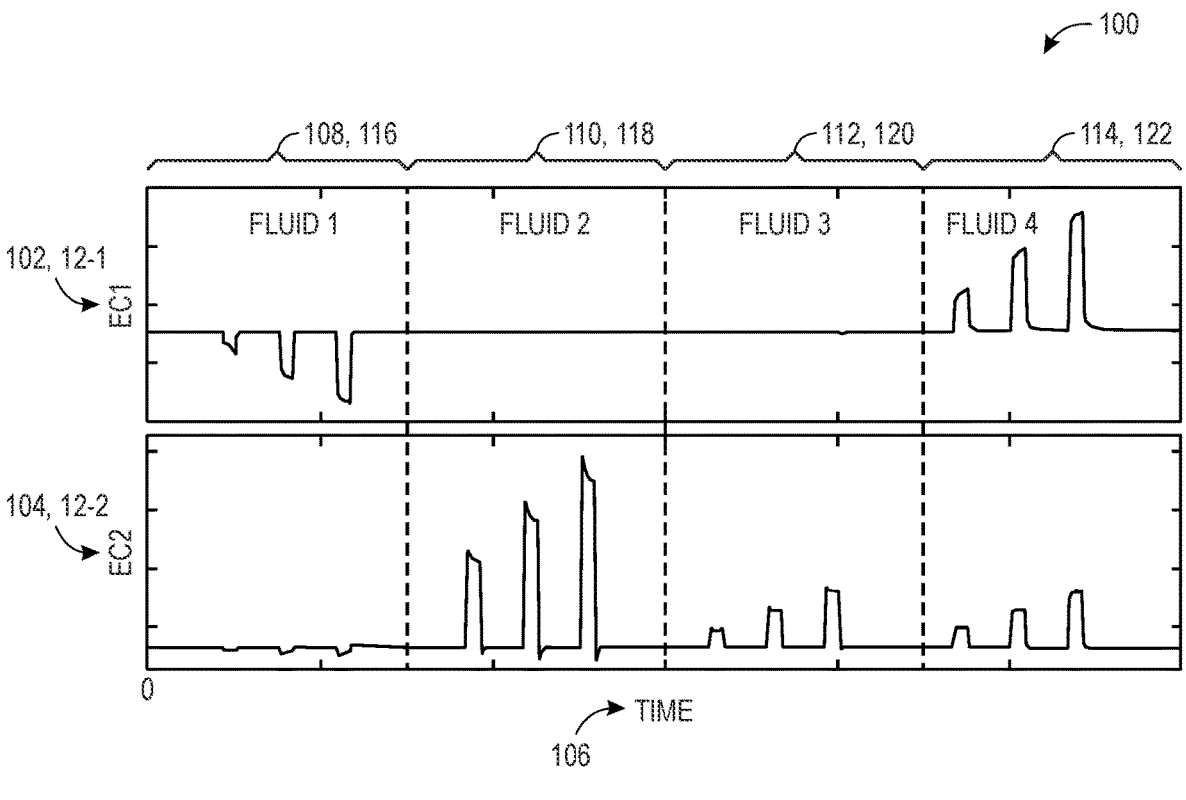
FIG. 4 illustrates a graph depicting example dynamic responses of the EC gas sensors of the sensor system of FIG. 1 in response to multiple different fluids, in accordance with one embodiment.

With the foregoing in mind, FIG. 4 illustrates a graph 100 depicting first EC response signals 102 of a first EC gas sensing element 12-1 and a second EC response signal 104 of a second EC gas sensing element 12-2. For example, the array 11 of FIG. 1 may include the first EC gas sensing element 12-1 and the second EC gas sensing element 12-2. Moreover, the measurement circuit 32 described above may generate stimulus signals over time 106. Furthermore, the first EC response signal 102 and the second EC response signal 104 may represent electrical current response of the EC gas sensing elements 12-1 and 12-2. The EC gas sensing elements 12-1 and 12-2 may generate an electrical current proportional to concentration of a detected gas. The gas is measured at the respective electrodes 20. In some embodiments, the EC gas sensing elements 12-1 and/or 12-2 may include a counter-electrode to complete the electrical circuit of the respective sensor cells. The processor 36 may apply (or provide control signals to apply) a voltage (e.g., one or more stimulus signals) at the respective electrodes 20 to provide a bias voltage or a bias potential of the EC gas sensing elements 12-1 and/or 12-2.

The first EC response signal 102 and the second EC response signal 104 may each include different responses to different gases (e.g., fluid patterns 108, 110, 112, and 114). For example, the first EC gas sensor sensing element 12-1 and the second EC gas sensing element 12-2 may be exposed to a first fluid over a first time period 116, a second fluid over a second time period 118, a third fluid over a third time period 120, and a fourth fluid over a fourth time period 122. The fluids I-4 of FIG. 4 may include Nitrogen Dioxide ($NO_2$), Carbon monoxide (CO), Diesel exhaust, and Hydrogen sulfide ($H_2S$), among other fluids. As shown in FIG. 4, each fluid may be presented to the sensors at three increasing concentrations. The analyte gases of interest were Nitrogen Dioxide (fluid 1), Carbon monoxide (fluid 2), and Hydrogen sulfide (fluid 4). The interferent was Diesel exhaust (fluid 3). The goal of sensor 10 was to differentiate between analyte gases (the fluids 1, 2, and 4) and the interferent gas (fluid 3).

In any case, as mentioned above, the EC gas sensing elements 12, such as the first EC gas sensing element 12-1 and the second EC gas sensing element 12-2, may provide the response signals 102 and 104 with more stability based on lower susceptibility to drifting values over time. As such, in some embodiments, the measurement circuit 32, the data processing unit 34, or both may determine the response signals 102 and 104 of the first EC gas sensing element 12-1 and the second EC gas sensing element 12-2 in the absence of the fluids 1-4 as baseline signals. Accordingly, the measurement circuit 32, the data processing unit 34, or both may correct the baseline responses of the MOS gas sensing elements 13 based on the response signals 102 and 104 of the first EC gas sensing element 12-1 and the second EC gas sensing element 12-2.

Figure 5:
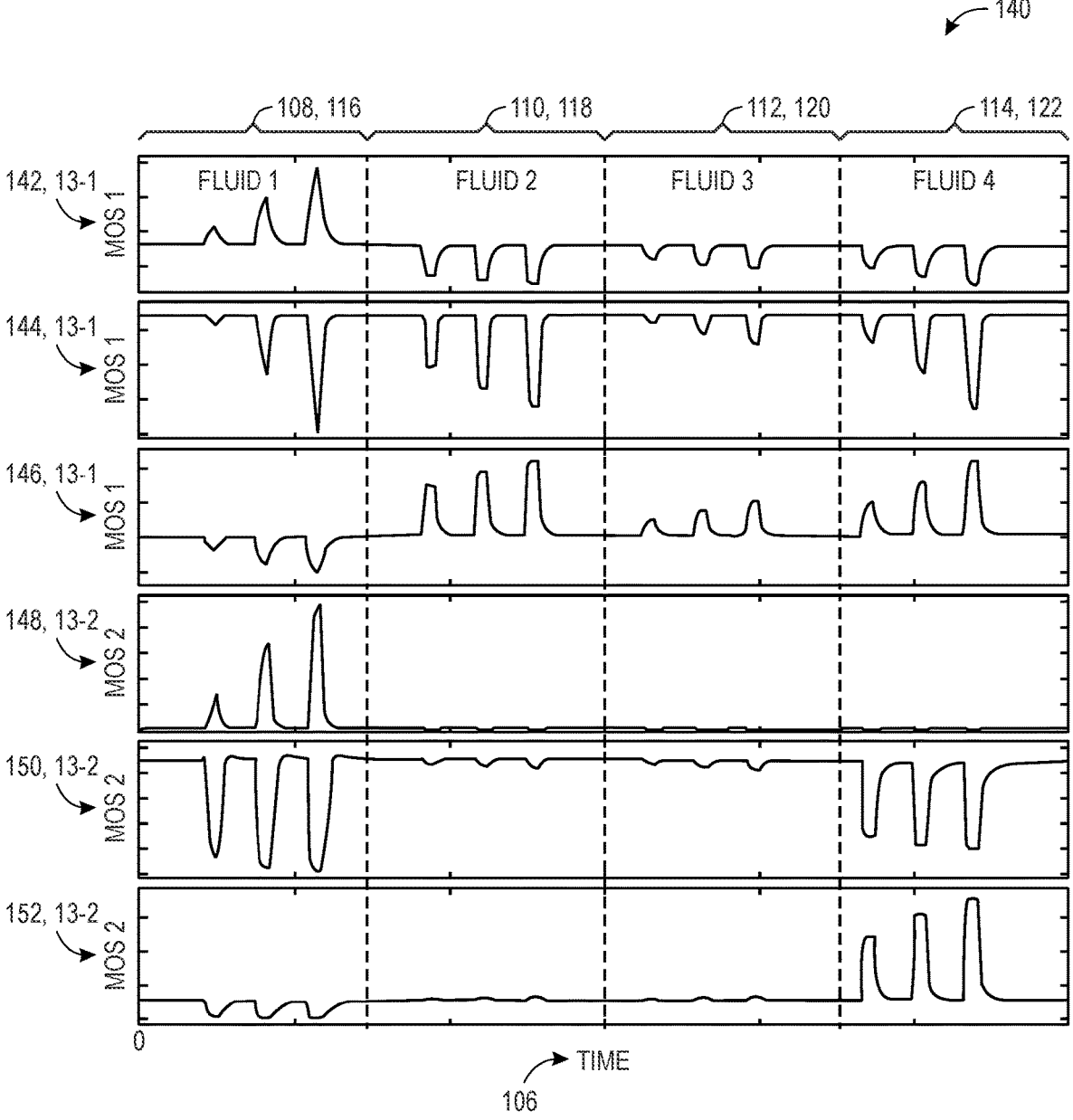
FIG. 5 illustrates a graph depicting example dynamic responses of MOS gas sensors of the sensor system of FIG. 1 in response to multiple different fluids when applying alternating current (AC) excitation with three different AC excitation frequencies, in accordance with one embodiment.

FIG. 5 illustrates a graph 140 depicting multiple MOS response signals of each of a first MOS gas sensing element 13-1 and a second MOS gas sensing element 13-2 of the array 11. In particular, the graph 140 includes a first MOS response signal 142, a second MOS response signal 144, and a third MOS response signal 146 of the first MOS gas sensing element 13-1. The graph 140 also includes a fourth MOS response signal 148, a fifth MOS response signal 150, and a sixth MOS response signal 152 of the second MOS gas sensing element 13-2. For example, one or more of the MOS response signals 142, 144, 146, 148, 150, and 152 may include impedance responses of the first MOS gas sensing element 13-1 and the second MOS gas sensing element 13-2 of the array 11. It should be appreciated that each of the MOS response signals 142, 144, 146, 148, 150, and 152 may represent a real part or an imaginary part of an impedance response at particular frequencies, among other parameters.

A multivariate response pattern may include results of analysis of graphs 100 and 140. In particular, the multivariate response pattern may include the first EC response signals 102 of a first EC gas sensing element 12-1, a second EC response signal 104 of a second EC gas sensing element 12-2, and the multiple MOS response signals of each of a first MOS gas sensing element 13-1 and a second MOS gas sensing element 13-2 of the array 11. The control circuitry 14 may determine an improved differentiation between gases in contact with the array 11, as compared to non-selected responses from the MOS gas sensing element 13 based on the multivariate response pattern. In some cases, the control circuitry 14 may determine the one or more gases in contact with the EC gas sensing element 12 and the MOS gas sensing element 13 by one or more multivariate statistical analysis tools such as PCA and/or HCA (e.g., unsupervised, supervised, etc.), as will be appreciated. For example, performing the multivariate statistical analysis of the one or more EC response signals 102 and/or 104 and the at least two MOS response signals 142, 144, 146, 148, 150, and/or 152 may provide an improved differentiation between the gases as compared to using non-selected responses from the sensor 10. The non-selected responses from the sensor 10 may include DC resistance responses of the MOS gas sensors (e.g., the MOS gas sensing element 13) as compared to AC impedance responses of the MOS gas sensing elements 13.

In the depicted example, the first MOS gas sensing element 13-1 and the second MOS gas sensing element 13-2 may each be exposed to the same fluid patterns 108, 110, 112, and 114 over similar respective time periods 116, 118, 120, and 122 as the EC gas sensing elements 12-1 and 12-2. For example, the results of the graphs 100 and 140 may be a result of simultaneous operations, consecutive operations, or otherwise correlated operations. Moreover, the measurement circuit 32 may generate stimulus signals with a different excitation frequency for each of the MOS response signals 142, 144, and 146 of the first MOS gas sensing element 13-1 and the MOS response signals 148, 150, and 152 of the second MOS gas sensing element 13-2.

As discussed above and shown in FIG. 5, the MOS gas sensing elements 13-1 and 13-2 may each provide different responses to different fluid patterns 108, 110, 112, and 114 when receiving the excitation signals at different frequencies and providing the corresponding response signals 142, 144, 146, 148, 150, and 152. The MOS gas sensing materials 23 of each of the MOS gas sensing elements 13-1 and 13-2 may provide a different response to different fluid patterns 108, 110, 112, and 114 at different frequencies. For example, the fifth MOS response signal 150 and the sixth MOS response signal 152 of the second MOS gas sensing element 13-2, each associated with a stimulus signal with a specific frequency, may provide a measurable response to the first fluid pattern 108 and the fourth fluid 114.

Similarly, the fourth MOS response signal 148 associated with a different stimulus frequency may provide a measurable response only to the first fluid pattern 108. In some embodiment, the processor 36 may use information (e.g., a lookup table) stored on the memory 38 to determine excitation frequency for providing the stimulus signals for detecting the fluid patterns 108, 110, 112, and 114 and/or a concentration of the respective fluid patterns 108, 110, 112, and 114. The processor 36, or any other viable circuitry, may determine the fluid patterns 108, 110, 112, and 114 and/or a concentration of the respective fluid patterns 108, 110, 112, and 114 by classification/cluster analysis and quantitation algorithms. Examples of classification/cluster analysis algorithms may include, but are not limited to, Principal Component Analysis (PCA), Hierarchical Cluster Analysis (HCA), Independent Component Analysis (ICA), Linear Discriminant Analysis (LDA), and Support Vector Machines (SVM) algorithm. Non-limiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), Support Vector Regression (SVR) or Artificial Neural Network Analysis (ANN), among other viable processes.

Figure 6:
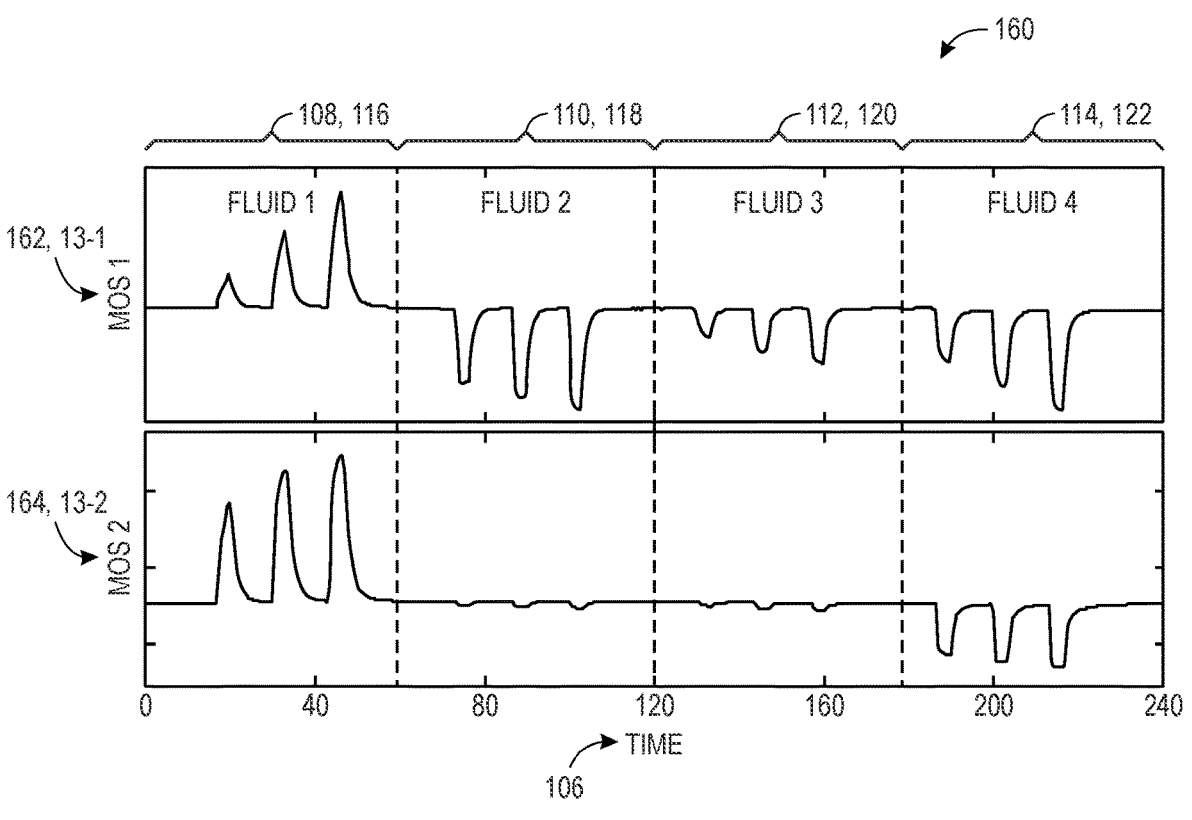
FIG. 6 illustrates a graph depicting example dynamic responses of the MOS gas sensors of FIG. 5 in response to multiple different fluids when applying the stimuli with a single direct current (DC) excitation for comparison, in accordance with one embodiment.

FIG. 6 depicts a graph 160 illustrating MOS resistance responses 162 and 164 of the MOS gas sensing elements 13-1 and 13-2 to the fluid patterns 108, 110, 112, and 114 when providing a direct current (DC signal) excitation signal (e.g., relatively close to zero Hertz) for comparison.

As shown in FIG. 5, each of the MOS gas sensing elements 13-1 and 13-2 may provide different responses to different fluid patterns 108, 110, 112, and 114 when providing the excitation signals at different frequencies. However, in some cases, when providing the excitation signals at a single zero frequency (e.g., DC signals), the MOS gas sensing elements 13-1 and 13-2 may each provide different responses (e.g., resistance responses) to different fluid patterns 108, 110, 112, and 114. For example, in FIG. 6, in the example of graph 160, the MOS gas sensing element 13-1 may provide MOS resistance responses 162 and 164 different from the MOS response signals 142, 144, 146, 148, 150, and 152 discussed above. In particular, the MOS resistance responses 162 and 164 depict changes of the resistance responses of the MOS gas sensing elements 13-1 and 13-2 when in contact with the fluids 110 and 112 in time periods 118 and 120. Accordingly, in such cases, it may be more desirable to provide multiple excitation signals at multiple different frequencies to the MOS gas sensing elements 13-1 and 13-2 such as the graph 140 of FIG. 5 described above.

Figure 7A:
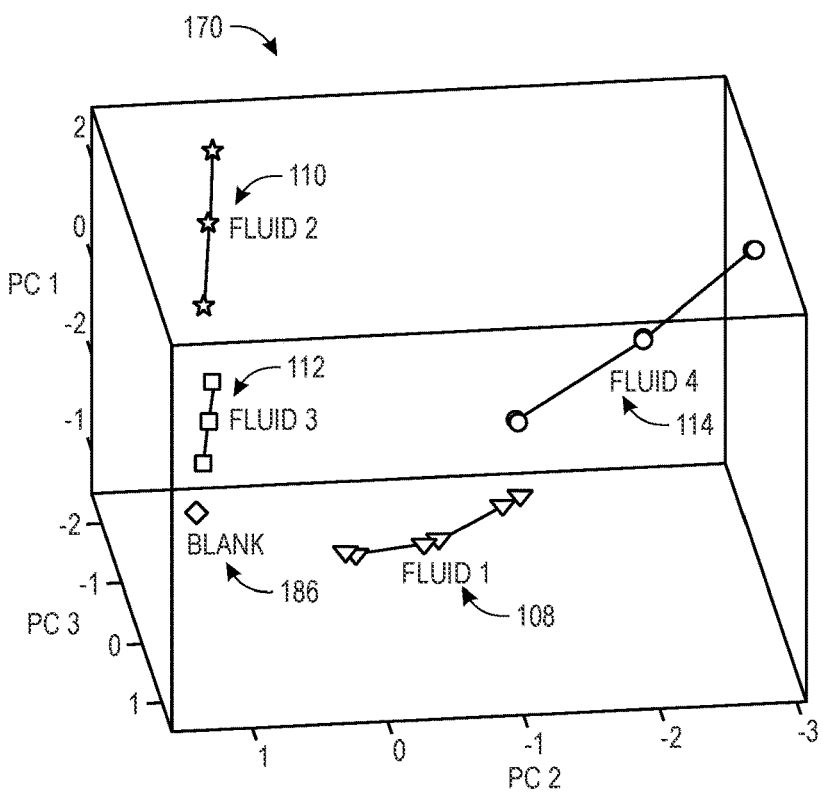
FIG. 7A is a first three-dimensional scores plot at a first visualization angle depicting principal component analysis (PCA) results of the combination of responses of the EC gas sensors and responses of the MOS gas sensors when applying the multiple stimuli with different AC excitation frequencies, in accordance with aspects of the present technique.
Figure 7B:
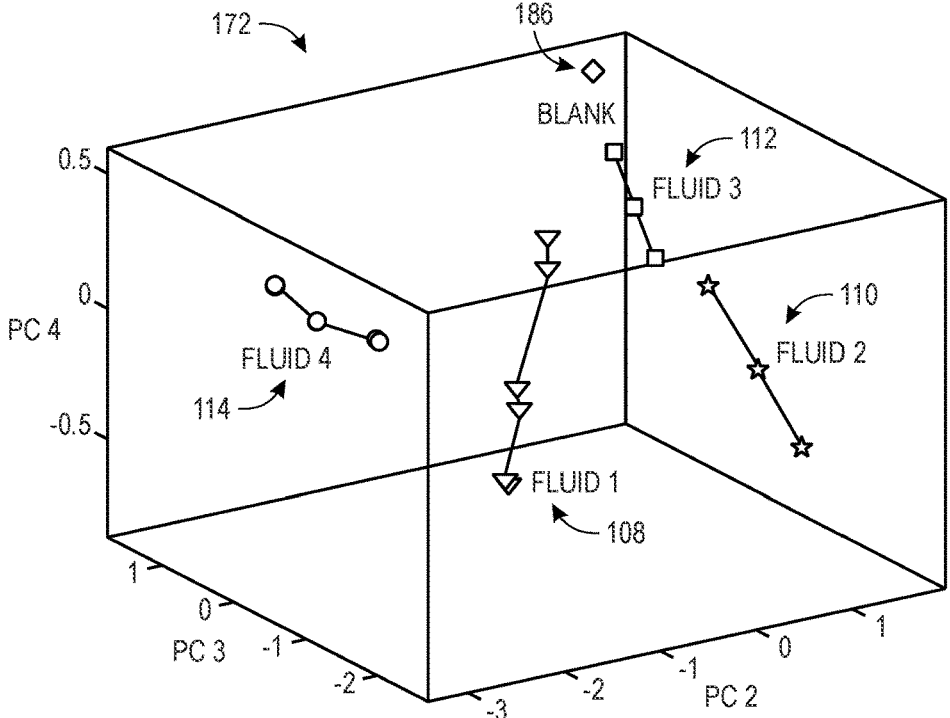
FIG. 7B is a second three-dimensional scores plot at a second visualization angle depicting PCA results of the combination of responses of the EC gas sensors and responses of the MOS gas sensors when applying the multiple stimuli with different AC excitation frequencies, in accordance with aspects of the present technique.

FIG. 7A is a first three-dimensional scores plot 170 at a first visualization angle depicting PCA results of the combination of responses of the EC gas sensing elements 12-1 and 12-2 and responses of the MOS gas sensing elements 13-1 and 13-2 when applying the stimuli with different AC excitation frequencies. Moreover, FIG. 7B is a first three-dimensional scores plot 172 at a second visualization angle depicting PCA results of the combination of responses of the EC gas sensing elements 12-1 and 12-2 and responses of the MOS gas sensing elements 13-1 and 13-2 when applying the stimuli with different AC excitation frequencies.

Figure 8A:
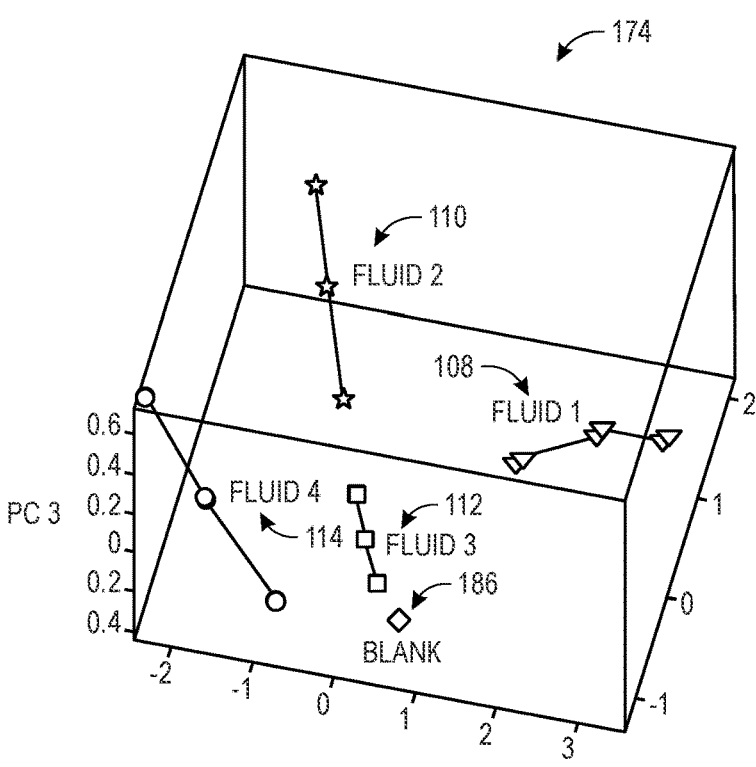
FIG. 8A is a three-dimensional scores plot at a first visualization angle depicting PCA results of the combination of responses of the EC gas sensors and responses of the MOS gas sensors when applying DC excitation for comparison, in accordance with aspects of the present technique.
Figure 8B:
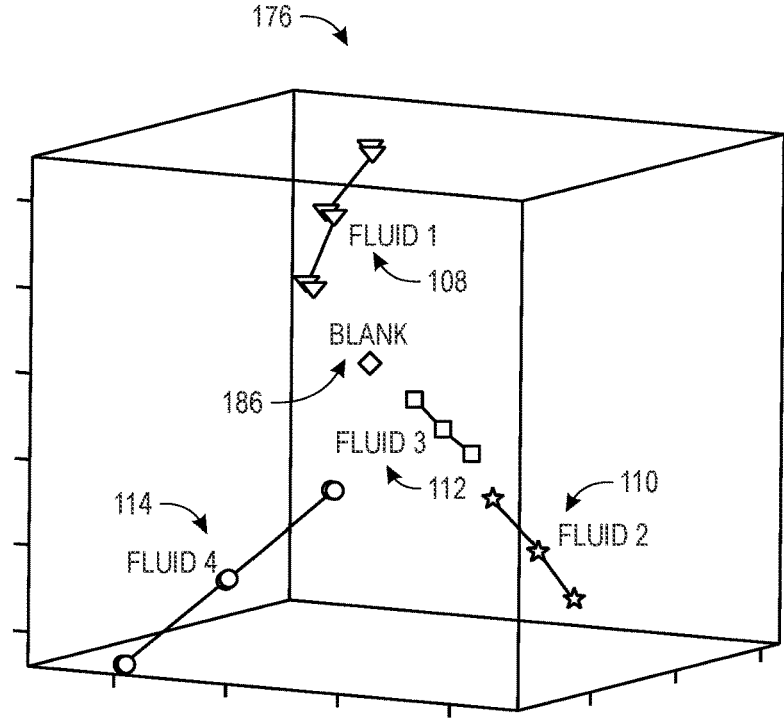
FIG. 8B is a three-dimensional scores plot at a first visualization angle depicting PCA results of the combination of responses of the EC gas sensors and responses of the MOS gas sensors when applying DC excitation for comparison, in accordance with aspects of the present technique

FIG. 8A is a three-dimensional scores plot 174 at a first visualization angle depicting PCA results of the combination of responses of the EC gas sensing elements 12-1 and 12-2 and responses of the MOS gas sensing elements 13-1 and 13-2 when applying DC excitation for comparison. Moreover, FIG. 8B is a three-dimensional scores plot 176 at a second visualization angle depicting PCA results of the combination of responses of the EC gas sensing elements 12-1 and 12-2 and responses of the MOS gas sensing elements 13-1 and 13-2 when applying DC excitation for comparison.

In some cases, the processor 36 may correct the baseline response of MOS gas sensing elements 13-1 and/or 13-2 by tracking the deviation of the baseline response of the MOS gas sensing element 13 from the baseline response of the EC gas sensing elements 12-1 and 12-2 as discussed above. The PCA results of the scores plots 170 and 172 provides more distinctive results based on the fluid patterns 108, 110, 112, and 114 compared to the PCA results of the scores plots 174 and 176. In one non-limiting example, the principal component (PC) results of the scores plots 170 and 172 show PC1 equal to 55.1%, PC2 equal to 24.04%, and PC3 equal to 18.64% while the principal component (PC) results of the scores plot 176 shows PC1 equal to 73.99%, PC2 equal to 22.41%, and PC3 equal to 3.21%.

Figure 9:
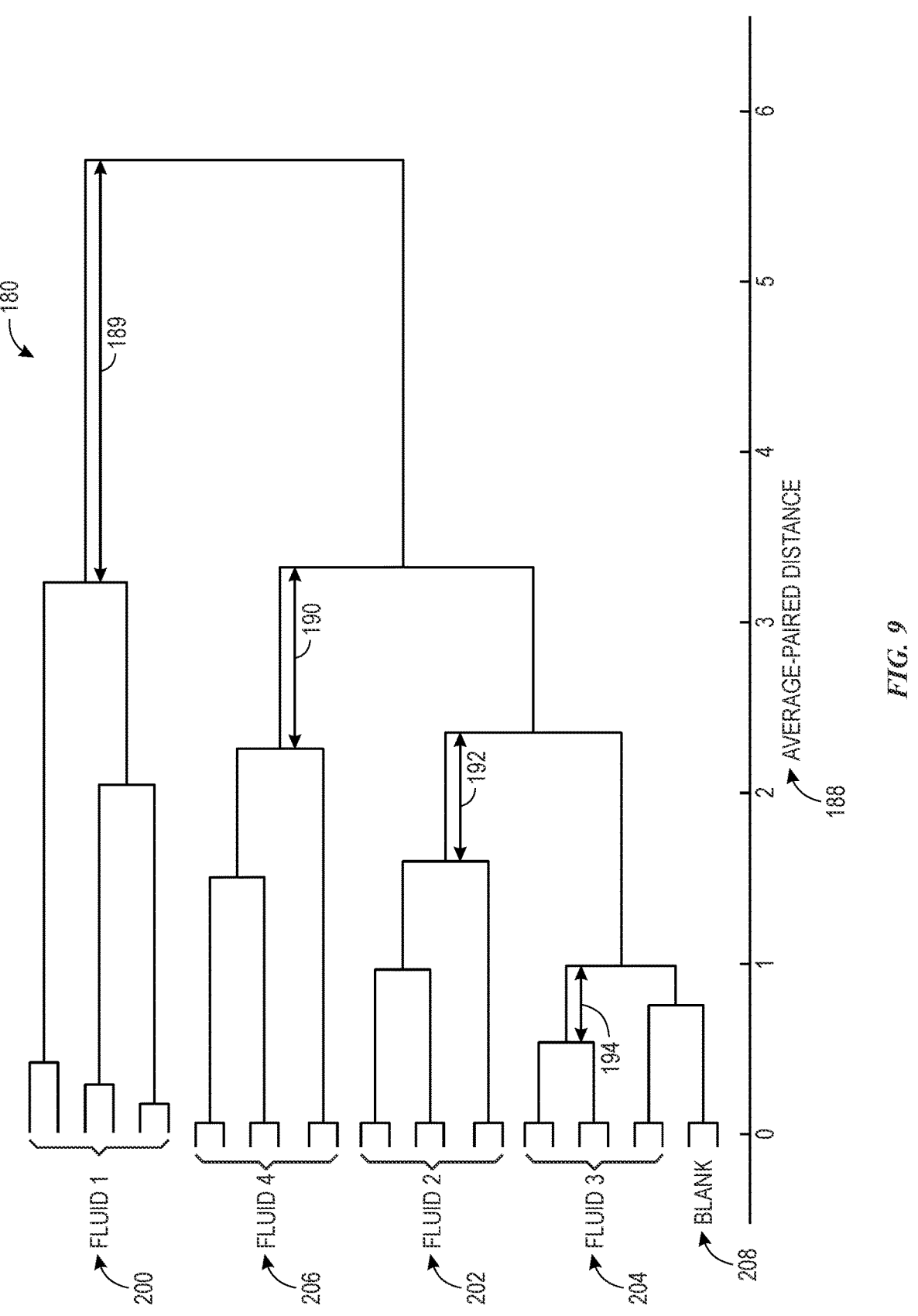
FIG. 9 is a dendrogram plot depicting hierarchical cluster analysis (HCA) results of the combination of responses of the EC gas sensors and responses of the MOS gas sensors when applying the multiple stimuli with different AC excitation frequencies, in accordance with aspects of the present technique.

FIG. 9 is a dendrogram plot 180 depicting hierarchical cluster analysis (HCA) results of the combination of responses of the EC gas sensing elements 12-1 and 12-2 and responses of the MOS gas sensing elements 13-1 and 13-2. For example, the EC gas sensing elements 12-1 and 12-2 and the MOS gas sensing elements 13-1 and 13-2 may provide the responses in response to the processor 36 applying the stimuli with different AC excitation frequencies of the MOS gas sensing elements 13-1 and 13-2. The dendrogram plot 180 may depict the hierarchical relationship between multivariable responses of the sensor 10 to the fluids I-4 (of FIGS. 4-6) at their respective concentrations (e.g., three concentration depicted in FIGS. 4-6).

The dendrogram plot 180 of FIG. 9 allocates the multivariable responses of the sensor 10 to the fluids 1-4 to different clusters based on the fluid types (or gas types). The vertical axis in FIG. 9 may represent hierarchical relationship of the samples in the analyzed data set which may include responses of sensor 10 sensing the fluids 1-4. For example, one or multiple clusters may be grouped to identify each of the fluids 1-4 based on the fluid clusters 200, 202, 204, and 206, and a blank cluster 208. The blank cluster 208 may be the baseline response of the sensor 10 in the absence of the fluids 1-4 in a clean air.

The horizontal axis 188 in FIG. 9 depicts the distances between response clusters 200, 202, 204, and 206 produced by the fluids 1-4 (and the blank cluster 208). The horizontal axis 188 may depict a magnitude of dissimilarities of one or more data sets associated with the response clusters 200, 202, 204, and 206 produced by the fluids 1-4 (and the blank cluster 208). As such, the dendrogram plot 180 may provide a hierarchical structure of a data set associated with the responses produced by the fluids 1-4 and the blank cluster 208.

In FIG. 9, the clusters 200, 202, 204, and 206 may depict responses to the fluids 1-4 at the respective concentrations (e.g., three concentrations) at one or two data points per each concentration. In alternative or additional embodiments, the clusters 200, 202, 204, and 206 may depict responses to the fluids 1-4 at the respective concentrations (e.g., three concentrations) at a different number of data points per each concentration.

In the depicted embodiment, the depicted cluster of the data set of the fluid clusters 200 associated with the fluid 1 may include a longest distance 189 compared to clusters of the fluid clusters 202, 204, and 206. For example, the response clusters to the fluids 4, 2, and 3 are depicted with shorter respective distances 190, 192, and 194 in the hierarchical order. The response cluster of the blank 186 may have the shortest distance.

Thus, the dendrogram plot 180 of FIG. 9 demonstrated that the sensor 10 differentiated well between the fluids 1-4. For example, the different fluids may include Nitrogen Dioxide (e.g., the fluid 1), Carbon monoxide (e.g., the fluid 2), and Hydrogen sulfide (the fluid 4). The sensor 10 also differentiated well between Diesel exhaust (e.g., the fluid 3) at its medium and highest concentrations and considered a same cluster while analyzing the small concentration of Diesel exhaust (e.g., the fluid 3) and the blank cluster 208. Thus, the response of sensor 10 analyzed by the HCA dendrogram plot in FIG. 9 demonstrated the desired differentiation between analyte gases (e.g., the fluids 1, 2, and 4) and the interferent gas (e.g., the fluid 3).

Figure 10:
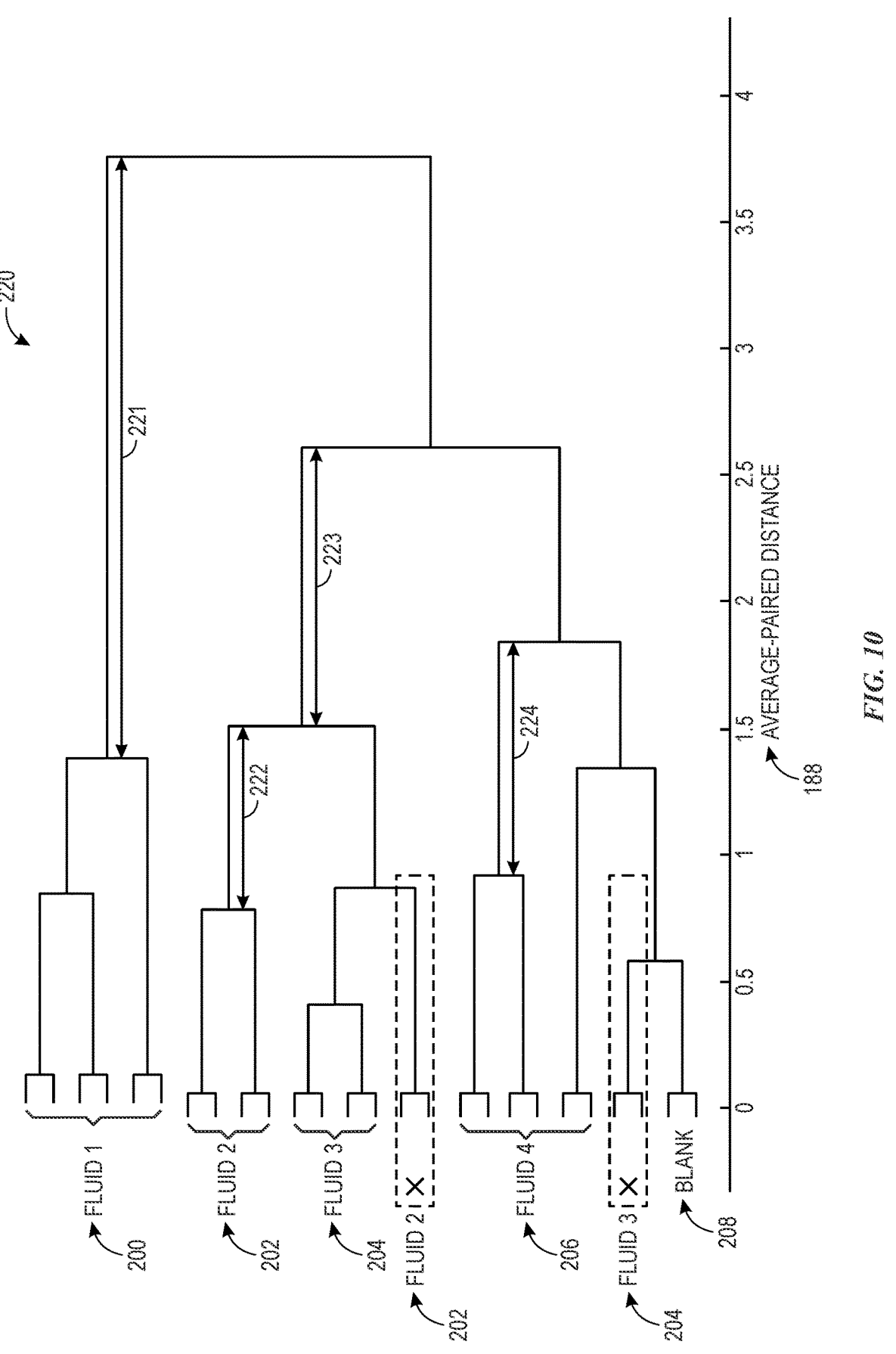
FIG. 10 is a dendrogram plot depicting HCA results of the combination of responses of the EC gas sensors and responses of the MOS gas sensors when applying DC excitation for comparison, in accordance with aspects of the present technique.

FIG. 10 is a dendrogram plot 220 depicting hierarchical cluster analysis (HCA) results of the combination of responses of the EC gas sensing elements 12-1 and 12-2 and responses of the MOS gas sensing elements 13-1 and 13-2 when applying DC excitation for comparison, in accordance with aspects of the present technique. The results demonstrate that the sensor 10 may produce erroneous clusters of Diesel exhaust (e.g., the fluid 3) and Carbon monoxide (e.g., the fluid 2). The results may also demonstrate that the sensor 10 produced another erroneous cluster of Hydrogen sulfide (e.g., the fluid 4), Diesel exhaust (e.g., the fluid 3), and the blank cluster 208. Thus, the response of the sensor 10 analyzed by the dendrogram plot 220 in FIG. 10 demonstrated lower differentiation between the analyte gas (e.g., the fluid 2) and the interferent gas (e.g., the fluid 3) and lower differentiation between analyte gas (e.g., the fluid 4) and the interferent gas (e.g., the fluid 3) compared to the dendrogram plot 180 of FIG. 9.

In FIG. 10, the depicted cluster of the data set of the fluid clusters 200 associated with the fluid 1 may include a longest distance 221 compared to clusters of the fluid clusters 202, 204, and 206. For example, the response clusters to the fluids 4, 2, and 3 are depicted with shorter respective distances 190, 192, and 194 in the hierarchical order. The response cluster of the blank 208 may have the shortest distance.

However, in comparison to the response clusters to the fluids 4, 2, and 3 that are depicted in FIG. 9 with shorter respective distances 190, 192, and 194 in the hierarchical order, response clusters to the fluids 4, 2, and 3 in FIG. 10 have some less ordered structure. The fluids 2 and 3 are separated by distance 222. Clusters of the fluids 2 and 3 is separated from the fluid 4 by distance 223. Two concentrations of the fluid 4 are separated by distance 224 from a cluster that contains one concentration of the fluid 4, one concentration of the fluid 3, and a blank 208.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled," "operationally contacted," "operational contact" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description.

The scope of the subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the present subject matter, and also to enable one of ordinary skill in the art to practice the embodiments of the disclosed subject matter, including making and using any devices or systems and performing any incorporated methods. The patentable scope of the subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor device comprising:
at least one electrochemical (EC) gas sensor;
at least one metal-oxide semiconductor (MOS) gas sensor; and
control circuitry configured to:
   provide one or more EC excitation signals to the at least one EC gas sensor;
   provide at least two MOS alternating current (AC) excitation signals to the at least one MOS gas sensor; and
   detect at least two gases based on:
      receiving a plurality of EC response signals from each EC gas sensor of the at least one EC gas sensor in response to each EC excitation signal of the provided one or more EC excitation signals;
      receiving at least two or more MOS response signals from each MOS gas sensor of the at least one MOS gas sensor based on providing the at least two MOS AC excitation signals;
      determining a multivariate response pattern based on the plurality of EC response signals and the at least two or more MOS response signals; and
      differentiating between the at least two gases in contact with the sensor device based on the multivariate response pattern.

2. The sensor device of claim 1, wherein the multivariate response pattern comprises the plurality of EC response signals from each EC gas sensor of the at least one EC gas sensor and the at least two or more MOS response signals from each MOS gas sensor of the at least one MOS gas sensor.

3. The sensor device of claim 1, wherein the at least one EC gas sensor comprises an EC gas sensing material and the at least one MOS gas sensor comprises a MOS gas sensing material.

4. The sensor device of claim 1, wherein the control circuitry comprises:
a controller coupled to the at least one EC gas sensor and the at least one MOS gas sensor configured to generate the one or more EC excitation signals and the at least two MOS AC excitation signals, and
a detector configured to receive the plurality of EC response signals and the at least two or more MOS response signals, wherein the detector comprises an electrical current detector, a resistance detector, an impedance detector, or a combination thereof.

5. The sensor device of claim 1, wherein detecting a first gas of the at least two gases is by correcting a baseline drift of the at least two or more MOS response signals based on the plurality of EC response signals.

6. The sensor device of claim 1, wherein the control circuitry differentiates between the at least two gases based on the multivariate response pattern by applying one or more supervised multivariate statistical analysis tools, one or more unsupervised multivariate statistical analysis tools, or both.

7. The sensor device of claim 1, comprising a memory storing one or more gas classification models to detect a first gas and a second gas based on differentiating the at least two gases.

8. The sensor device of claim 7, wherein the memory stores one or more gas quantitation models associated with detecting a concentration of the first gas, the second gas, or both.

9. The sensor device of claim 1, wherein the control circuitry receives:

control signals indicative of one or more operation parameters of the at least one MOS gas sensor, the at least one EC gas sensor, or both; and one or more values for each of the one or more operation parameters before providing the one or more EC excitation signals to the at least one EC gas sensor and providing the at least two MOS AC excitation signals to the at least one MOS gas sensor.

10. The sensor device of claim 9, wherein the one or more operation parameters comprise a real part of impedance, an imaginary part of the impedance, frequency, or a combination thereof, of the one or more EC excitation signals, the at least two MOS AC excitation signals, or both.

11. The sensor device of claim 1, wherein the control circuitry comprises one or more processors, where the one or more processors are configured to determine one or more gas types and at least one gas concentration of the at least two gases.

12. The sensor device of claim 11, wherein the one or more processors are configured to generate control signals indicative of performing at least one responsive action based on determining the one or more gas types and the at least one gas concentration.

13. The sensor device of claim 12, wherein the responsive action comprises generating one or more alerts, activation of an emergency response, activation of a particular treatment or decontamination of a subject having the sensor device, optimization of logistics steps after a knowledge about a detected concentration of the at least two gases, minimization of logistics steps after the knowledge about the detected concentration of the at least two gases, or a combination thereof.

* * * * *